(12) United States Patent  
Mullen et al.

(10) Patent No.: US 12,055,518 B2
(45) Date of Patent: Aug. 6, 2024

(54) LIQUID CHROMATOGRAPHY-MASS SPECTROMETRY (LC-MS) METHODS FOR ANALYZING AMPHOLYTE LOT VARIATION

(71) Applicant: Regeneron Pharmaceuticals, Inc., Tarrytown, NY (US)

(72) Inventors: Rachel Mullen, East Greenbush, NY (US); Clare Ryan, Wynantskill, NY (US); Seamus O'Connor, Ballston Lake, NY (US); Stacey Helming, Troy, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 688 days.

(21) Appl. No.: 17/067,044

(22) Filed: Oct. 9, 2020

(65) Prior Publication Data

US 2021/0109063 A1    Apr. 15, 2021

Related U.S. Application Data

(60) Provisional application No. 62/913,450, filed on Oct. 10, 2019.

(51) Int. Cl.
| | |
|---|---|
| *G01N 27/447* | (2006.01) |
| *G01N 30/72* | (2006.01) |
| *G01N 30/86* | (2006.01) |
| *G16C 20/20* | (2019.01) |
| *G01N 30/02* | (2006.01) |

(52) U.S. Cl.
CPC ....... *G01N 27/44795* (2013.01); *G01N 30/72* (2013.01); *G01N 30/8624* (2013.01); *G16C 20/20* (2019.02); *G01N 2030/027* (2013.01)

(58) Field of Classification Search
None
See application file for complete search history.

(56) References Cited

U.S. PATENT DOCUMENTS

| | | |
|---|---|---|
| 6,107,623 A | 8/2000 | Bateman et al. |
| 6,124,137 A | 9/2000 | Hutchens et al. |
| 6,204,500 B1 | 3/2001 | Whitehouse et al. |
| 6,268,144 B1 | 7/2001 | Köster |

(Continued)

FOREIGN PATENT DOCUMENTS

| | | |
|---|---|---|
| CN | 106932459 A | 7/2017 |
| EP | 3143392 A1 | 3/2017 |

(Continued)

OTHER PUBLICATIONS

Čabovska, B., "Application of Multivariate Analysis and LC-MS for the Detection of Counterfeit Cosmetics," Waters Corporation, May 2015, pp. 1-5, retrieved from https://www.waters.com/webassets/cms/library/docs/720005402en.pdf.

(Continued)

*Primary Examiner* — Xiaoyun R Xu
(74) *Attorney, Agent, or Firm* — COOLEY LLP

(57) ABSTRACT

The disclosure relates to methods of characterizing ampholyte compositions suitable for downstream applications such as capillary isoelectric focusing using liquid-chromatography-mass spectrometry.

25 Claims, 14 Drawing Sheets

(12 of 14 Drawing Sheet(s) Filed in Color)

(56) References Cited

U.S. PATENT DOCUMENTS

| | | | |
|---|---|---|---|
| RE42,025 E | * | 1/2011 | Melby .................. C08F 220/56 526/287 |
| 2008/0128606 A1 | | 6/2008 | Grant et al. |
| 2015/0115151 A1 | * | 4/2015 | Verenchikov ....... H01J 49/0031 250/281 |
| 2017/0234852 A1 | | 8/2017 | Feng et al. |
| 2019/0056350 A1 | | 2/2019 | Rambhadran et al. |

FOREIGN PATENT DOCUMENTS

| | | | | |
|---|---|---|---|---|
| EP | 3514545 A1 | | 7/2019 | |
| JP | 2004117200 A | | 4/2004 | |
| JP | 2021515242 A | | 6/2021 | |
| WO | WO 2016/115561 | * | 7/2016 | ............. A61K 47/12 |
| WO | WO-2018064091 A1 | | 4/2018 | |
| WO | WO-2019141422 A1 | | 7/2019 | |
| WO | WO-2021072230 A1 | | 4/2021 | |

OTHER PUBLICATIONS

Felten et al., "Imaged Capillary Isoelectric Focusing for Charge-Variant Analysis of Biopharmaceuticals," BioProcess International, Nov. 1, 2011, 10 pages, retrieved from https://bioprocessintl.com/analytical/product-characterization/imaged-capillary-isoelectric-focusing-for-charge-variant-analysis-of-biopharmaceuticals-323451/.

Poitevin et al., "Comparison of different capillary isoelectric focusing methods-use of "narrow pH cuts" of carrier ampholytes as original tools to improve resolution," Journal of Chromatography A, 2007, 1155, 230-236.

Sebastiano et al., "Mass distribution and focusing properties of carrier ampholytes for isoelectric focusing: I. Novel and unexpected results," Electrophoresis, 2006, 27, 3919-3934.

Silvertand et al., "Recent developments in capillary isoelectric focusing," Journal of Chromatography A, 2008, 1204, 157-170.

Fujimura, Y., et al., "Application of LC/MS-based Metabolic Profiling Evaluation of Health-promoting Function of Agricultural Products", Shimadzu, Application Note No. 32, (2012) [online] https://www.an.shimadzu.co.jp/sites/an.shimadzu.co.jp/files/pim/pim_document_file/an_jp/applications/application_note/18528/ap_aplnote32-jp.pdf; 8 pages.

* cited by examiner

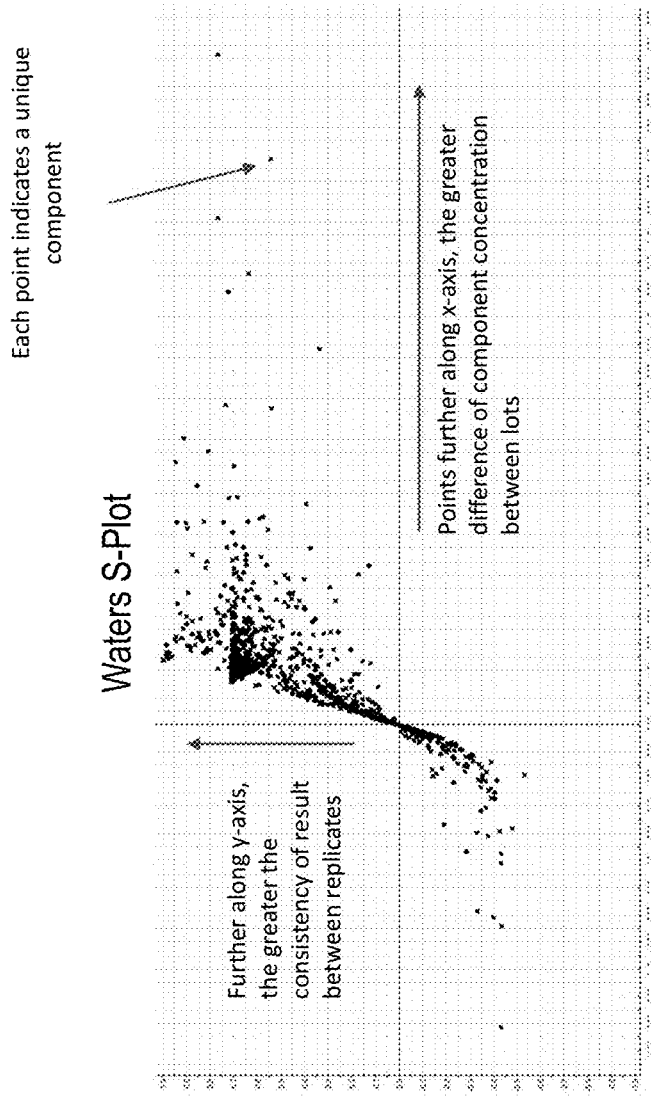

| m/z value | Lot Number | | | | |
|---|---|---|---|---|---|
| | 1 | 2 | 3 | 4 | 5 |
| 280 | 100% | 65% | 35% | 16% | 24% |
| 319 | 94% | 100% | 50% | 59% | 61% |
| 329 | 100% | 47% | 40% | 46% | 43% |
| 347 | 100% | 67% | 50% | 31% | 25% |
| 373 | 90% | 100% | 85% | 94% | 60% |
| 375 | 100% | 85% | 43% | 41% | 38% |
| 376 | 100% | 92% | 50% | 42% | 25% |
| 431 | 100% | 65% | 65% | 53% | 7% |
| 504 | 100% | 87% | 73% | 100% | 67% |
| 506 | 100% | 100% | 71% | 85% | 71% |
| 508 | 68% | 68% | 62% | 100% | 49% |
| 520 | 100% | 80% | 49% | 54% | 58% |
| 534 | 100% | 100% | 59% | 50% | 40% |
| 562 | 100% | 79% | 46% | 40% | 34% |
| 906 | 24% | 30% | 28% | 100% | 18% |
| 980 | 67% | 94% | 100% | 33% | 53% |

LIQUID CHROMATOGRAPHY-MASS SPECTROMETRY (LC-MS) METHODS FOR ANALYZING AMPHOLYTE LOT VARIATION

CROSS-REFERENCE TO RELATED APPLICATIONS

This application claims the benefit of priority to U.S. Provisional Patent Application Ser. No. 62/913,450 filed on Oct. 10, 2019, the contents of which are hereby incorporated by reference in their entirety.

TECHNICAL FIELD

The disclosure relates to methods of characterizing protein compositions by charge, and characterizing ampholyte compositions using liquid chromatography-mass spectrometry (LC-MS).

BACKGROUND

Many proteins undergo secondary modifications that cause protein charge variants, such as deamidation, formation of N-terminal pyroglutamate, aggregation, isomerization, sialylated glycans, fragmentation, and glycation at the lysine residues. In some cases, these secondary modifications and charge variants arising therefrom can affect binding, biological activity, patient safety, and shelf life of the protein. Tools such as isoelectric-focusing gel electrophoresis (IEF), and capillary equivalents such as capillary isoelectric focusing (CIEF) and imaged CIEF (iCIEF) can be used to analyze the charge of proteins. These techniques are important for characterizing and monitoring quality, purity, stability and variability of therapeutic proteins such as protein based drug products and drug substances. One such technique, iCIEF, has contributed significantly to biopharmaceutical development with its high resolution, minimal development time, reduced sample volume, and fast run times. Those benefits allow for applications across entire pharmaceutical processes, from cell culture development and optimization to commercial quality control (QC) release and stability activities.

In CIEF and iCIEF, separation of proteins with different net charges is accomplished by focusing the proteins in an ampholytic pH gradient through an applied electric field, separating isoforms based on intrinsic isoelectric charge. This separation technique relies on ampholytes to create a pH gradient when placed under an electric potential. Protein species then migrate to different regions on the capillary based on their isoelectric point, or pI value. However, lot-to-lot variation in the ampholyte compositions used to generate the pH gradient in these methods can affect assay results. Previous methods of characterizing ampholyte compositions for their suitability for iCIEF and similar techniques have relied on indirect methods, such as using ampholyte compositions to generate iCIEF electropherograms or similar readouts of a reference protein, and comparing the resulting electropherograms generated by different ampholyte compositions. However, these methods are costly, time consuming, and use large quantities of protein. There thus exists a need in the art for improved methods of characterizing ampholyte compositions for their suitability in methods such as iCIEF. This invention meets this need by providing improved methods to directly analyze ampholyte compositions.

SUMMARY

The disclosure provides methods of identifying a test ampholyte composition with suitable activity, comprising: (a) identifying at least one marker in at least one test ampholyte composition and a reference ampholyte composition using liquid chromatography-mass spectrometry (LC-MS); and (b) determining the degree of similarity or difference of the at least one marker between the at least one test ampholyte composition and the reference ampholyte composition, wherein the at least one test ampholyte composition has suitable activity if the at least one marker has a low covariance and the level of the at least one marker is different between the at least one test ampholyte composition and the reference ampholyte composition, or wherein the at least one test ampholyte composition has suitable activity if the at least one marker has a high covariance and the level of the at least one marker is similar between the at least one test ampholyte composition and the reference ampholyte composition; thereby identifying a test ampholyte composition with suitable activity.

In some embodiments of the methods of the disclosure, step (a) comprises (i) determining Accurate Mass/Retention Time (AMRT) or collision cross section (CCS) measurements for a plurality of components of the at least one test ampholyte composition and the reference ampholyte composition; (ii) plotting covariance of the AMRT or collision cross section measurements for the plurality of components from the at least one test and reference ampholyte compositions using an S-plot; and (iii) selecting at least one component that is different between the at least one test ampholyte composition and the reference ampholyte compositions, wherein the difference comprises a covariance that is non-0 in the S-plot; thereby identifying at least one marker for characterizing the suitability of the at least one test ampholyte composition. In some embodiments, the difference comprises a covariance that is less than 0 in the S-plot. In some embodiments, the at least one component comprises a covariance in the S-plot that is less than the covariance of at least 20%, at least 30%, at least 40%, at least 50%, at least 60%, at least 70%, or at least 80% of the plurality of components in the S-plot. In some embodiments, the at least one test ampholyte composition has suitable activity if the level of the at least one marker in the at least one test ampholyte composition and the reference ampholyte composition is different.

In some embodiments of the methods of the disclosure, the difference in the level of the at least one marker comprises a difference in level of at least 10%, at least 20%, at least 30%, at least 40%, at least 50%, at least 60%, at least 70%, at least 80%, or at least 90% relative to a normalized level of the at least one marker.

In some embodiments of the methods of the disclosure, step (a) comprises (i) determining Accurate Mass/Retention Time (AMRT) or collision cross section measurements for a plurality of components of the at least one test ampholyte composition and the reference ampholyte composition; (ii) plotting covariance of the AMRT or collision cross section measurements for the plurality of components from the at least one test and reference ampholyte compositions using an S-plot; and (iii) selecting at least one component that is similar between the at least one test ampholyte composition and the reference ampholyte compositions, wherein the similarity comprises a covariance that is non-0 in the S-plot; thereby identifying at least one marker for characterizing the suitability of the at least one test ampholyte composition. In some embodiments, the difference comprises a covariance that is greater than 0 in the S-plot. In some embodiments, the at least one component comprises a covariance in the S-plot that is greater than the covariance of at least 40%, at least 50%, at least 60%, at least 70%, at least 80%, at least 90%, at least 95%, or at least 99% of the plurality of components in the S-plot. In some embodiments, the at least one test ampholyte composition has suitable activity if the level of the at least one marker in the at least one test ampholyte composition and the reference ampholyte composition is similar.

In some embodiments of the methods of the disclosure, the similarity in the level of the at least one marker comprises a level that is at least 20%, at least 30%, at least 40%, at least 50%, at least 60%, at least 70%, at least 80%, at least 90%, at least 95% or at least 99% similar relative to a normalized level of the at least one marker.

In some embodiments of the methods of the disclosure, the at least one marker is identified by a mass to charge ratio (m/z). In some embodiments, the level of the at least one marker is characterized by relative intensity of the m/z in a mass spectrum.

In some embodiments of the methods of the disclosure, step (b) comprises: (i) determining a LC-MS mass spectrum of the at least one marker in the at least one test ampholyte composition and the reference ampholyte composition, (ii) determining the relative intensity of a base peak for the at least one marker in the mass spectrums of the at least one test ampholyte composition and the reference ampholyte composition, (iii) normalizing the relative intensity of the base peak of the at least one marker to a maximum relative intensity of the base peak measured from the at least one test ampholyte composition or the reference ampholyte composition, and (iv) comparing the normalized relative intensities of the base peak of the at least one marker in the at least one test and reference ampholyte compositions.

In some embodiments of the methods of the disclosure, the at least one marker comprises 1, 2, 3, 4, 5, 6, 7, 8, 9, 10, 11, 12, 13, 14, 15 or 16 markers with different m/z. In some embodiments, the at least one marker comprises 16 markers with different m/z. In some embodiments, the 16 markers comprise markers with an m/z of 280, an m/z of 319, an m/z of 329, an m/z of 347, an m/z of 373, an m/z of 375, an m/z of 376, an m/z of 431, an m/z of 504, an m/z of 506, an m/z of 508, an m/z of 520, an m/z of 534, an m/z of 562, an m/z of 906 and an m/z of 980.

In some embodiments of the methods of the disclosure, the mass spectrometry comprises ion mobility Quadrupole Time-of-flight Mass Spectrometry (IMS-Q-ToF-MS).

In some embodiments of the methods of the disclosure, the liquid chromatography comprises high-performance liquid chromatography (HPLC). In some embodiments, the HPLC comprises a C4 silica column.

In some embodiments of the methods of the disclosure, the methods further comprise validating the at least one test ampholyte composition by generating an imaged capillary isoelectric focusing (iCIEF) electropherogram of a reference protein using the reference ampholyte composition and the at least one test ampholyte composition, thereby generating at least one test electropherogram and a reference electropherogram.

In some embodiments of the methods of the disclosure, the test ampholyte composition is validated if the at least one test and the reference electropherograms are similar. In some embodiments, the similarity of the at least one test and reference electropherograms is determined by number, size, or isoelectric point (pI) of peaks, or a combination thereof.

In some embodiments of the methods of the disclosure, the suitable activity comprises capillary isoelectric focusing (CIEF) or imaged capillary isoelectric focusing (iCIEF). In some embodiments, the iCIEF is used to characterize a protein drug product or drug substance.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A uses ampholyte lot 1. FIG. 1B shows an exemplary candidate ampholyte lot, which generates a different electropherogram profile from the same Reference Protein than the ampholyte lot shown in FIG. 1A. Differences in electropherograms are circled.

FIG. 5A shows an exemplary electropherogram with two peaks. FIG. 5B illustrates how resolution is calculated from the electropherogram. Resolution is calculated based on migration (run) time (Rt) and peak width (W). FIG. 5C shows an exemplary electropherogram in which there is 0.15% mutual overlap between peaks, or a Resolution of 1.5, which is the chromatographic minimum criteria.

FIG. 8A is a table showing GE Healthcare IEF carrier ampholyte lots tested for their molecular components.

FIG. 8B is a Waters S-Plot showing testing of ampholyte lots for their molecular composition variation, rather than performance. Liquid chromatography-mass spectrometry (LC-MS) was used to identify components of interest in ampholyte lots that have a high degree of variation between lots. Analysis was performed using UNIFI software with built in data analysis and workflows. The S-plot shows the Accurate Mass/Retention Time (AMRT) dissimilarities between lots of ampholytes. AMRT pairs are plotted by covariance, with the magnitude of the change shown on the x-axis and correlation, i.e. the consistency of the change, shown on the y-axis.

FIG. 9A shows a comparison of lots 1 and 2. FIG. 9B shows a comparison of lots 1 and 3. FIG. 9C shows a comparison of lots 1 and 5. The Waters S-plot identifies similarities and differences between the samples, and provides a powerful visual filtering tool. Unique features were selected for a library of ampholyte components, for example the highlighted points in the lot 1 vs lot 5 S-plot (FIG. 9C) were selected.

DETAILED DESCRIPTION

Figure 1A:
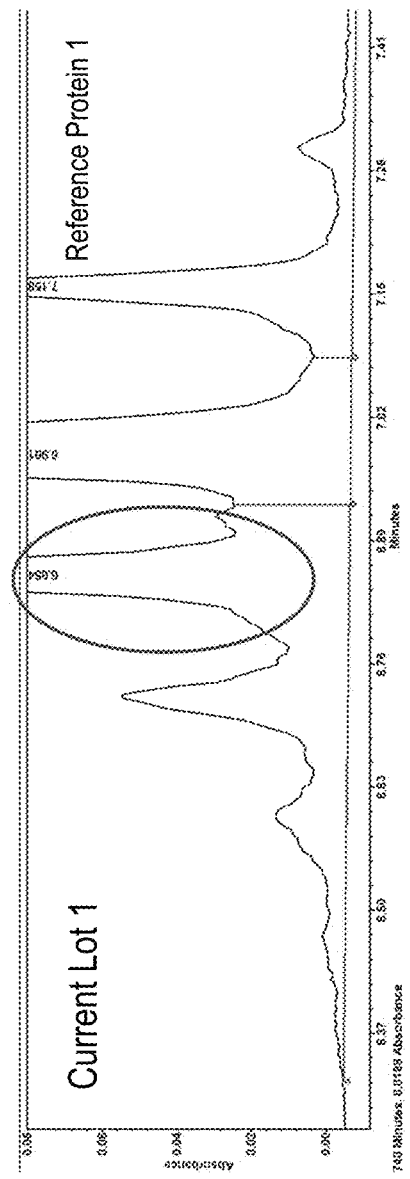
FIGS. 1A-1B are a pair of electropherograms analyzing a Reference Protein product using an imaged Capillary Isoelectric Focusing (iCIEF) assay. The x-axis shows time (in minutes), while the y-axis shows absorbance.

The disclosure provides methods of identifying ampholyte compositions with suitable activity for desired downstream applications, comprising: (a) identifying at least one marker in at least one test ampholyte composition and a reference ampholyte composition using liquid chromatography-mass spectrometry (LC-MS); and (b) determining the degree of similarity or difference of the at least one marker between the at least one test ampholyte composition and the reference ampholyte composition. In some embodiments, markers are chosen based on differences between a reference and test ampholyte composition, and the at least one test ampholyte composition has suitable activity if the at least one marker is different between the at least one test ampholyte composition and the reference ampholyte composition. In some embodiments, markers are chosen based on similarities between a reference and test ampholyte composition, and the at least one test ampholyte composition has suitable activity if the at least one marker is similar between the at least one test ampholyte composition and the reference ampholyte composition. Markers can be identified by a specific mass to charge ratio (m/z) measured via mass spectrometry, and levels or markers can be determined by the relative intensity of the indicated m/z peak, which can optionally be normalized. This normalization can be to the maximum relative intensity measured for the indicated m/z peak across ampholyte compositions in the analysis. Markers can be further characterized by retention time in the liquid chromatography separation step.

Suitable activities for downstream applications include, but are not limited to, isoelectric-focusing gel electrophoresis (IEF), and capillary equivalents such as capillary isoelectric focusing (CIEF) and imaged CIEF (iCIEF).

In some embodiments, the methods further comprise validating the at least one test ampholyte composition by generating an imaged capillary isoelectric focusing (iCIEF) electropherogram of a reference protein using the reference ampholyte composition and the at least one test ampholyte composition, thereby generating at least one test electropherogram and a reference electropherogram. Similarity of test and reference electropherograms can be determined by comparing number, size, area, resolution, and isoelectric point (pI) of the peaks of the reference and test electropherograms, or a combination thereof of all of these characteristics.

Uses of Ampholyte Compositions

The disclosure provides methods for determining the suitability of ampholyte compositions for one or more downstream applications.

Ampholyte compositions, sometimes referred to as pharmalytes (e.g., commercially produced ampholytes from GE Healthcare), are used for a variety of methods that separate proteins based on isoelectric charge. Exemplary methods for which ampholyte compositions can be optimized using the methods described herein include, but are not limited to, isoelectric-focusing gel electrophoresis (IEF), and capillary equivalents such as capillary isoelectric focusing (CIEF) and imaged CIEF (iCIEF).

As used herein, "ampholytes" refers to compounds containing both positive and negative charges that behave as zwitterions at and near their isoelectric point (pI) values. An ampholyte can act as an acid or a base, depending on the pH of the solution into which it is introduced. Ampholytes assist in the formation of pH gradients, for example during focusing in iCIEF and CIEF.

The isoelectric point (pI) is the pH at which a molecule carries no net electrical charge. For a protein, the isoelectric point is the pH at which the overall charge of the protein is zero.

Isoelectric-Focusing Gel Electrophoresis (IEF).

IEF is a technique for separating proteins based on charge that involves adding an ampholyte solution to an immobilized pH gradient (IPG) gel. IPGs comprise an acrylamide gel matrix co-polymerized with a pH gradient, which can be generated by embedding carrier ampholytes in the acrylamide matrix. The resulting pH gradients are stable in an electric field, except at highly alkaline (>12) pH values. The pH gradient for protein separation is fully established before adding the protein analytes by first subjecting a solution of small molecules such as polyampholytes with varying pI values to electrophoresis.

When an electric field is applied, a protein that is in a pH region below its isoelectric point (pI) will be positively charged and so will migrate toward the cathode (negatively charged electrode). As it migrates through a gradient of increasing pH, overall charge of the protein will decrease until the protein reaches the pH region that corresponds to its pI. At this point it has no net charge and so migration ceases (as there is no electrical attraction toward either electrode). As a result, the proteins become focused into sharp stationary bands with each protein positioned at a point in the pH gradient corresponding to its pI.

Capillary Isoelectric Focusing (CIEF) and Imaged Capillary Isoelectric Focusing (iCIEF)

Capillary Isoelectric Focusing (CIEF) and Imaged Capillary Isoelectric Focusing (iCIEF) are analytic techniques used separate protein variants primarily on the basis of the protein's isoelectric (pI) intrinsic net charge. In CIEF and iCIEF, sample separation is conducted by focusing protein samples in an ampholytic pH gradient through an applied electric field. Protein samples are premixed with carrier ampholytes, additives and pI markers. The protein samples are then separated in a capillary cartridge with electrolytic tanks at each end. One tank is filled with acid (anolyte) and the other base (catholyte). The sample mixture is injected to fill the capillary column, and voltage is applied to the anolyte and catholyte tanks. This creates a pH gradient, which separates and focuses the proteins (analytes) based on their pI along the capillary.

In CIEF, the focusing step is followed by a mobilization step, in which the focused analytes are moved along the capillary to a capillary outlet and past a detector such as a UV or fluorescence detector. Mobilization methods include hydrodynamic or pressure mobilization, i.e. by applying a gas to the capillary, and chemical mobilization, in which the anolyte or catholyte is replaced with a different electrolyte solution with a high ionic strength or different pH.

In contrast to CIEF, which involves mobilizing protein samples across a detector, in iCIEF, a whole-column detector, such as a UV or fluorescence detector, monitors the entire process across the capillary in real time. This allows for a close monitoring of the focusing step, followed by an instant final charge variant profile. Advantages of iCIEF over other techniques include thus include high resolution, efficient run time, and low sample consumption, making it a preferred technique for protein characterization in the biopharmaceutical industry.

Variability and Ampholyte Compositions

The output of CIEF or iCIEF analysis of a protein can be an electropherogram. In an electropherogram, the x-axis shows isoelectric point or mobilization time. The y-axis shows the readout of the detector, typically in absorbance units. Peaks in the electropherogram are sometimes referred to as absorbance peaks. Variation in ampholyte compositions can cause variability in output electropherograms.

Electropherograms of a reference protein generated using a test ampholyte composition can have one or more of the following changes relative to an electropherogram of the same reference protein generated with a reference ampholyte composition: (1) gain of one or more peaks, (2) loss of one or more peaks, (3) shifts in the pI or mobilization time of more or more peaks, (4) changes in the area under the peak of one or more peaks, and (4) changes in the resolution of one or more peaks.

Accordingly, the disclosure provides methods of determining if a test ampholyte composition will produce an electropherogram of a reference protein similar to the electropherogram of the same reference protein produced by a reference ampholyte. In some embodiments, the methods comprise (a) identifying at least one marker in at least one test ampholyte composition and a reference ampholyte composition using liquid chromatography-mass spectrometry (LC-MS); and (b) determining the degree of similarity or difference of the at least one marker between the at least one test ampholyte composition and the reference ampholyte composition, wherein the at least one test ampholyte composition has suitable activity if the at least one marker has a low covariance and the level of the at least one marker is different between the at least one test ampholyte composition and the reference ampholyte composition, and wherein the at least one test ampholyte composition has suitable activity if the at least one marker has a high covariance and the level of the at least one marker is similar between the at least one test ampholyte composition and the reference ampholyte composition; thereby identifying a test ampholyte composition with suitable activity.

The disclosure further provides methods of validating the activity of ampholyte compositions characterized using the methods described herein, comprising generating electropherograms using the reference ampholyte composition and at least one test composition, and comparing the electropherograms to determine if they are similar.

In some embodiments, similarity of the at least one test and reference electropherograms is determined by number, size, resolution, isoelectric point (pI) of the peaks or a combination thereof.

In some embodiments, similar electropherograms have a similar or identical number of peaks (for example, the number of peaks varies by 3, 2, 1, or 0 peaks). As a further example, both the test and reference electropherogram comprise or consist essentially of 1, 2, 3, 4, 5, 6, 7, 8, 9, 10, 11, 12, 13, 14, 15, 16, 17, 18, 19 or 20 peaks.

In some embodiments, similarity of the at least one test and reference electropherograms comprises similar resolution.

Figure 5A:
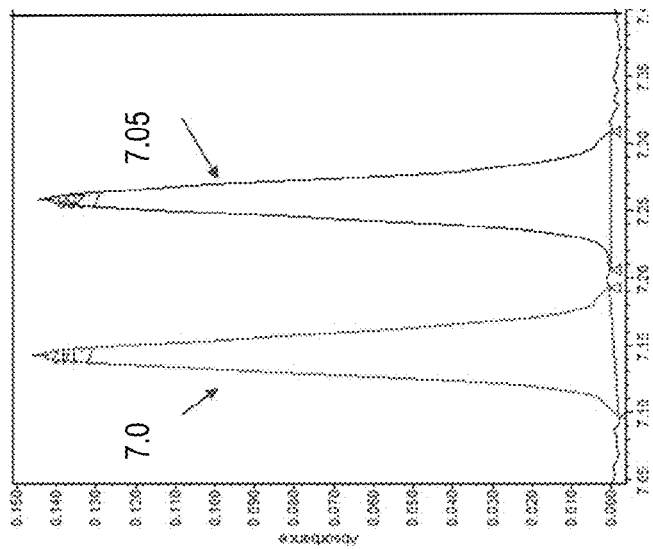
FIGS. 5A-5C are a series of plots showing isoelectric point (PI, or pI) marker testing of ampholytes lots. The resolution of peaks with each ampholyte lot was calculated between 7.0 and 7.05.
Figure 5B:
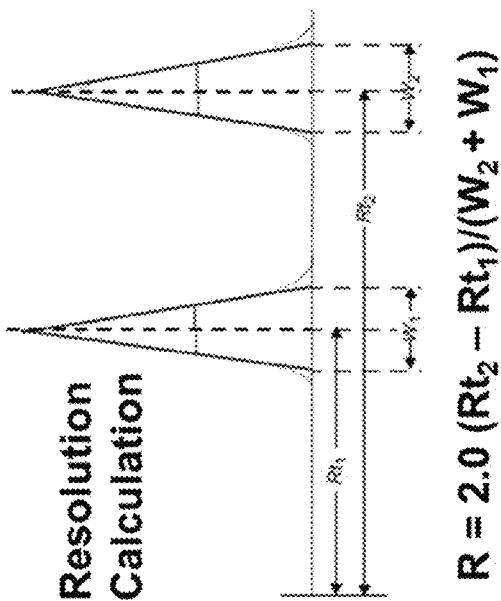
Figure 5C:
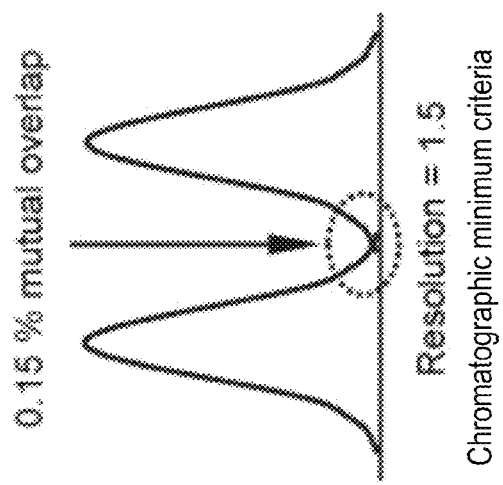
Figure 6:
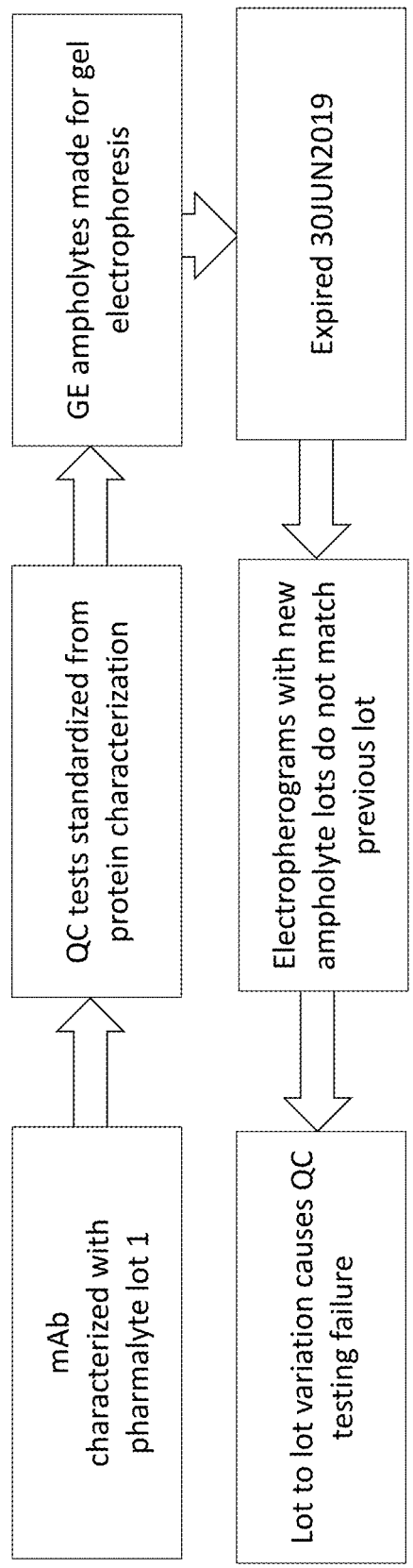
FIG. 6 is a diagram outlining a problem solved by the methods of the instant disclosure.

As used herein, "resolution" or "R" is a measure of the quality of a separation, for example the separation of a pair of absorbance peaks in an electropherogram. Methods of calculating resolution between two peaks are shown in FIGS. 5A-5C. A resolution of 1.5 (0.15% mutual overlap) is considered a baseline separation of two peaks and the chromatographic minimum criteria. The greater the resolution, the better the separation of the two peaks. Resolution is a combination of two factors, selectivity and efficiency of separation. Selectivity takes into account the distance between the maxima of the two peaks. Higher efficiency of separation occurs with narrower peaks. Therefore, narrow peaks and large peak-to-peak separations produce large R values. The calculation of resolution uses the difference in migration time or pI of the two peaks ($Rt_1$, $Rt_2$) and the base width of the peaks ($W_1$, $W_2$).

In some embodiments, the similarity of the test and reference electropherograms comprises a difference in resolution of less than 0.30, less than 0.25, less than 0.20, less than 0.175, less than 0.15, less than 0.13, less than 0.12, less than 0.11, less than 0.10, less than 0.08, less than 0.075, less than 0.07, less than 0.05, less than 0.03, less than 0.02 or less than 0.01. In some embodiments, the similarity of the test and reference electropherograms comprises a difference in resolution of less than 0.075. In some embodiments, the similarity of the test and reference electropherograms comprises a difference in resolution of less than 0.072.

In some embodiments, the similarity of the test and reference electropherograms comprises one or more peaks in a region of the electropherogram with similar areas. In some embodiments, the difference in area of the one or more peaks in a specific region of the test and reference electropherograms has a probability value (p-value) of less than or equal to 0.05. Methods of calculating the area under a peak will be known to persons or ordinary skill in the art, and include, for example, fitting an equation for a curve to the peak and integrating to find the area enclosed. In some embodiments, specific regions of the reference and test electropherograms whose peak areas are calculated can be defined by specific pI markers included in the analyte mix. In some embodiments, specific regions of the reference and test electropherograms whose peak areas are calculated can be defined by the presence of major peak common across electropherograms. For example, an electropherogram can be divided into the major peak, and areas that are acidic or basic relative to the major peak.

Significance can be determined by calculating p-value, or probability value, which is the probability that the null model (for example, that two peaks would have the same area by chance) would be true. Methods of calculating p-values will be known to persons of ordinary skill in the art, and include Student's t-test, Chi-square test, analysis of variance (ANOVA), Pearson correlation coefficient and Bonferroni-Dunn. In some embodiments, a result is thought to be significant if the p value is less than 0.05. In some embodiments, a result is thought to be significant if the p value is less than 0.04, less than 0.03, less than 0.02 or less than 0.01.

In some embodiments, the difference in area of the one or more peaks in a specific region of the test and reference electropherograms has a coefficient of variation (% RSD) of less than or equal to 5%. Percent RSD is defined as the ratio of the standard deviation to the mean, and shows the extent of variability in relation to the mean of a population (for example, replicates of an electropherogram). Methods of calculating percent RSD will be known to persons of ordinary skill in the art. In some embodiments, a dataset is reproducible if the % RSD is less than 5%. In some embodiments, a dataset is reproducible if the % RSD is less than 4%, less than 3%, less than 2% or less than 1%.

Characterizing Ampholyte Compositions Using Liquid Chromatography-Mass Spectrometry (LC-MS)

Provided herein are methods of characterizing ampholyte compositions using liquid chromatography-mass spectrometry (LC-MS). In some embodiments, the methods comprise identifying at least one marker in at least one test ampholyte composition and a reference ampholyte composition using liquid chromatography-mass spectrometry (LC-MS); and determining the degree of similarity or difference of the at least one marker between the at least one test ampholyte composition and the reference ampholyte composition. The at least one marker can be identified by MS mass to charge ratio (m/z) discussed below, and levels of the at least one marker determined by relative intensity as measured by MS for each marker of a given m/z. In some embodiments, the methods comprise identifying a plurality of markers in at least one test ampholyte composition and a reference ampholyte composition using liquid chromatography-mass spectrometry (LC-MS); and determining the degree of similarity or difference of the plurality of markers between the at least one test ampholyte composition and the reference ampholyte composition.

Liquid chromatography-mass spectrometry (LC-MS) is an analytical chemistry technique that combines the physical separation capabilities of liquid chromatography (for example, high performance liquid chromatography, or HPLC) with the mass analysis capabilities of mass spectrometry (MS). Liquid chromatography separates mixtures with multiple components, while mass spectrometry provides structural identity and levels of the individual components with high molecular specificity and detection sensitivity.

Liquid chromatography and mass spectrometry are described in EP3143392, the contents of which are incorporated herein by reference.

As used herein, the term "chromatography" refers to a process in which a chemical mixture comprising a liquid or gas is separated into components as a result of differential distribution of the chemical entities as they flow around, over, and/or through a stationary liquid or solid phase. "Liquid chromatography" or "LC" refers to a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Liquid chromatography includes, but is not limited to, reverse phase liquid chromatography (RPLC), high performance liquid chromatography (HPLC), high turbulence liquid chromatography (HTLC) and ultra performance liquid chromatography. "Retention time" refers to length of time for which a particular analyte, such as an ampholyte composition component, is retained by a liquid chromatography substrate prior to elution.

As used herein, the term "high performance liquid chromatography" or "HPLC" refers to liquid chromatography in which the degree of separation is increased by forcing the mobile phase under pressure through a stationary phase, typically a densely packed column.

As used herein the term "ultra performance liquid chromatography" or "UPLC" refers to liquid chromatography methods with enhanced speed, sensitivity and resolution as compared to HPLC. Generally, UPLC is applicable for particles of less than 2 µm in diameter. Separation and quantification in UPLC is done under extremely high pressure (up to 100 M Pa).

Gas chromatography (GC) refers to a separation technique that uses gas flowing through a column, such as a glass or metal column, to separate compounds based on volatility and interaction with a liquid stationary phase. The mobile phase, a carrier gas, is usually an inert gas such as helium or an unreactive gas such as nitrogen.

Mass spectrometry is performed using a mass spectrometer, which includes an ion source for ionizing a sample and creating charged molecules for further analysis. In various embodiments, ampholyte compositions and components thereof may be ionized by any method known to the skilled artisan. Ionization sources used in various MS techniques include, but are not limited to, electron ionization, chemical ionization, electrospray ionization (ESI), photon ionization, atmospheric pressure chemical ionization (APCT), photoionization, atmospheric pressure photoionization (APPI), fast atom bombardment (FAB)/liquid secondary ionization (LSIMS), matrix assisted laser desorption ionization (MALDI), field ionization, field desorption, thermospray/plasmaspray ionization, surface enhanced laser desorption ionization (SELDI), inductively coupled plasma (ICP), particle beam ionization and ion-mobility separation (IMS). The skilled artisan will understand that the choice of ionization method may be determined based on the analyte to be measured, type of sample, the type of detector, the choice of positive versus negative mode, etc.

As used herein, the term "mass spectrometry" or "MS" refers to an analytical technique to identify compounds by their mass. MS refers to methods of filtering, detecting, and measuring ions based on their mass to charge ratio (m/z). MS technology generally includes ionizing the compounds to form charged species (e.g., ions) and detecting the exact mass of the ions divided by their charge, known as m/z. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. Nos. 6,204,500; 6,107,623; 6,268,144; and 6,124,137.

MS can generate and detect both positive and negative ions. As used herein, the term "ionization" or "ionizing" refers to the process of generating an analyte ion having a net electrical charge equal to one or more electron units. Positive ions are those having a net positive charge of one or more electron units. Negative ions are those having a net negative charge of one or more electron units. In "electron ionization" or "EI" methods, analytes in a gaseous or vapor phase interact with a flow of electrons. Impact of the electrons with the analyte produces analyte ions, which may then be subjected to mass spectrometry techniques. EI can be combined with gas chromatography (GC) or liquid chromatography methods. In "chemical ionization" or "CI," a reagent gas (e.g. ammonia) is subjected to electron impact, and analyte ions are formed by the interaction of reagent gas ions and analyte molecules. In "fast atom bombardment" or "FAB," a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyJ alcohol, 18-crown-6 crown ether, 2-nitropheiiy-loctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules. MALDI-TOF refers to Matrix-Assisted Laser Desorption/Ionization-Time Of Flight (MALDI-TOF) mass spectrometry (MS). MALDI-TOF is useful for compounds up to about 15,000 daltons.

"Surface enhanced laser desorption ionization" or "SELDI" refers to another method in which a non-volatile sample is exposed to laser irradiation, which desorbs and ionizes analytes in the sample by various ionization pathways, including photoionization, protonation, deprotonation, and cluster decay. For SELDI, the sample is typically bound to a surface that preferentially retains one or more analytes of interest. As in MALDI, this process may also employ an energy-absorbing material to facilitate ionization.

"Electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

"Atmospheric pressure chemical ionization" or "APCI," refers to mass spectroscopy methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "Atmospheric Pressure Photoionization" or "APPI" as used herein refers to the form of mass spectroscopy where the mechanism for the photoionization of molecule M is photon absorption and electron ejection to form the molecular M+. Because the photon energy typically is just above the ionization potential, the molecular ion is less susceptible to dissociation.

As used herein, the term "inductively coupled plasma" or "ICP" refers to methods in which a sample is interacted with a partially ionized gas at a sufficiently high temperature to atomize and ionize most elements.

As used herein, "ion-mobility spectrometry," sometimes also referred to as "ion-mobility separation" or "IMS" refers to an analytical chemistry method that separates gas phase ions based on their interaction with a collision gas and their masses. In the first step, the ions are separated according to their mobility through a buffer gas on a millisecond timescale using an ion mobility spectrometer. The separated ions are then introduced into a mass analyzer in a second step where their mass to charge ratios can be determined on a microsecond timescale.

As used, herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase.

After the ampholyte composition or components thereof have been ionized, the ions thereby created may be analyzed to determine m/z. Suitable analyzers for determining m/z include quadrupole analyzers, ion trap analyzers, time-of-flight analyzers, Fourier-transform ion cyclotron resonance (FTICR) analyzers and Orbitrap spectrometers. The ions may be detected using one of several detection modes. For example, only selected ions may be detected using a selective ion monitoring mode (SIM), or alternatively, multiple ions may be detected using a scanning mode, e.g., multiple reaction monitoring (MRM) or selected reaction monitoring (SRM).

In some embodiments, m/z is determined using a quadrupole analyzer (instrument). In a "quadrupole" or "quadrupole ion trap" instrument, ions in an oscillating radio frequency field experience a force proportional to the DC potential applied between electrodes, the amplitude of the RF signal, and m/z. The voltage and amplitude may be selected so that only ions having a particular m/z travel the length of the quadrupole, while all other ions are deflected. Thus, quadrupole instruments may act as both a "mass filter" and as a "mass detector" for the ions injected into the instrument. In Time-of-Flight (ToF), the ions are accelerated in a homogenous electrostatic field using ground and repeller electrodes. The kinetic energy is held constant, and the ion travel down the field-free ToF tube. Because kinetic energy is constant ($KE=\frac{1}{2}MV^2$) those with smaller m/z will have a greater speed compared to larger m/z. "Quadrupole time-of-flight" or "QTof" mass spectrometry refers to a type of mass spectrometry using mass spectrometers that pair a quadrupole that functions as a collision cell with a time-of-flight analyzer. This allows for high-resolution, high mass accuracy analysis of all ions simultaneously. In an exemplary QTof system, a sample is delivered by an online liquid chromatography system and ionized. The particle beam then travels through an ion guide and into the quadrupole, before passing to a ToF analyzer. In some embodiments, the MS technique can employ "tandem mass spectrometry," or "MS/MS." In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan or mass spectrum; that is, the relative abundance of each ion with a particular m/z over a given range (e.g., 400 to 1600 m/z). The mass spectrum may be related to the amount of the analyte, e.g. a component of an ampholyte composition, in the sample by numerous methods known in the art. For example, given that sampling and analysis parameters are carefully controlled, the relative abundance, sometimes referred to as relative intensity, of a given ion may be compared to a table that converts that relative abundance to an absolute amount of the original molecule. Alternatively, molecular standards may be run with the samples and a standard curve constructed based on ion signal generated from those standards. Methods of generating and using such standard curves are well known in the art and one of ordinary skill is capable of selecting an appropriate internal standard. Numerous other methods for relating the amount of an ion to the amount of the original molecule will be well known to those of ordinary skill in the art.

As ions collide with the detector they produce a pulse of electrons that are converted to a digital signal. The acquired data is relayed to a computer, which plots ion counts per unit time. The areas under the peaks corresponding to particular ions, or the amplitude of such peaks, are measured and the area or amplitude is correlated to the amount of the component of interest, or marker, in the ampholyte composition. In certain embodiments, the area under the curves, or amplitude of the peaks, for fragment ion(s) and/or precursor ions are measured to determine the amount of analytes with a given m/z. As described above, the relative abundance, sometimes referred to as relative intensity, or the response of a given ion may be converted into an absolute amount of the original analyte using calibration standard curves based on peaks of one or more ions of an internal molecular standard. The absolute amount of an ampholyte composition component detected by LC-MS can then be converted into an absolute amount of the component that was present in the original sample.

Relative abundance, or relative intensity, can also be defined as the y-axis of a mass spectrum. In some embodiments, the amount of a marker can be quantified in relation to the amount of the most abundant ion (the base peak) of the mass spectrum. In some embodiments, the amount of a marker can be quantified using a response factor or a standard curve. In some embodiments, quantifying the amount of a marker comprises (1) including an internal standard in the sample, for example the reference ampholyte and/or test ampholyte composition, and (2) normalizing the marker to the internal standard in the sample. In some embodiments, quantifying the amount of a marker further comprises (3) normalizing said marker to the maximum corrected amount of the marker as measured across multiple ampholyte compositions. For example, the marker can be normalized to the maximum corrected response (aka relative intensity) of the marker measured from multiple ampholyte lots from the same manufacturer. Internal standards include, but are not limited to $^{13}C_6$-carbamazepine, which elutes mid-run and has high ionization efficiency.

In some embodiments, the response of the internal standard can be used to normalize the response values for each m/z to account for instrument drift.

In some embodiments, the change in retention time (RT), collisional cross section (CCS), or both, and the m/z of the internal standard over the course of a run can be used to set the tolerances on the parameters for marker assignment.

In some embodiments, the relative intensity of a marker or component of an ampholyte composition is normalized, for example to the maximum relative intensity of that marker as measured across multiple ampholyte compositions.

As used herein, "accurate mass," sometimes referred to as the "measured accurate mass" is an experimentally determined mass from MS that allows the elemental composition of an analyte such as an ampholyte composition component to be determined. "Accurate Mass/Retention Time" or "AMRT" refers to the combination of (1) the retention time of a component of an ampholyte composition during liquid chromatography and (2) the accurate mass of the component as measured via mass spectrometry.

As used herein, "collision cross section" or CCS data can be obtained through ion mobility experiments. It is the effective area for the interaction between an individual ion and a neutral gas molecule, and relates to the characteristics of an ion such as chemical structure and dimensions. It can be derived using methods such as drift tube ion mobility measurements or traveling wave IMS. For example, multiple measurements are made at different electrical fields to calculate CCS values.

In some embodiments, the LC-MS comprises ultra high performance liquid chromatography tandem ion mobility quadrupole time of flight mass spectrometry (UPLC-IMS-Q-Tof MS).

Suitable LC-MS instruments and systems include, but are not limited to, the BioAccord LC-MS System for Biopharmaceuticals (Waters), the Waters Acquity UPLC H-Class combined with a Waters Vion IMS-Q-ToF-MS, the Agilent Ultivo LC/MS system, and Orbitrap LC-MS systems (ThermoFisher).

Determining Markers for Ampholyte Compositions

The disclosure provides methods of identifying at least one marker in an ampholyte composition comprising (i) determining Accurate Mass/Retention Time (AMRT) measurements or collision cross section measurements for a plurality of components of the at least one test ampholyte composition and the reference ampholyte composition; (ii)

plotting covariance of the AMRT measurements for the plurality of components from the at least one test and reference ampholyte compositions using an S-plot; and (iii) selecting at least one component that is either different between the at least one test ampholyte composition and the reference ampholyte composition, or selecting at least one component that is similar between the at least one test ampholyte composition and the reference ampholyte composition, thereby identifying at least one marker for characterizing the suitability of the at least one test ampholyte composition.

Similarities and differences between AMRT measurements of ampholyte composition components can be determined by any statistical method known in the art. One approach involves calculating and plotting the covariance of AMRT pairs between components of the at least one test ampholyte composition and the reference composition. Covariance, as used herein, refers to the joint variability of two random variables. If the greater values of one variable mainly correspond with the greater values of the other variable, and the same holds for the lesser values, (i.e., the variables tend to show similar behavior), the covariance is positive. In the opposite case, when the greater values of one variable mainly correspond to the lesser values of the other (i.e., the variables tend to show opposite behavior), the covariance is negative.

Covariance can be calculated using methods such as Principle Component Analysis (PCA), Orthogonal Projection to Latent Structures—Discrimination Analysis (OPLS-DA), and Waters S-plot, which will be known to persons of ordinary skill in the art.

"Principal component analysis" or "PCA" is a statistical procedure that uses an orthogonal transformation to convert a set of possibly correlated variables into a set of values of linearly uncorrelated variables called principal components. This transformation is defined in such a way that the first principal component has the largest possible variance (that is, accounts for as much of the variability in the data as possible), and each succeeding component in turn has the highest variance possible under the constraint that it is orthogonal to the preceding components. PCA thus allows for reducing large sets of multivariate data into uncorrelated variables known as principal components. PCA is limited in that no information about individual sample groups can be ascertained from the plot.

In some embodiments, data can be further mined using an orthogonal projection to latent structures—discrimination analysis (OPLS-DA). This statistical analysis allows for identifying specific features (e.g., ampholyte species) that contribute to the overall differences observed between two groups.

In some embodiments, the PCA and optionally, OPLS-DA data can be viewed as an S-plot. An S-plot is a statistical method of plotting dissimilarities seen between two groups of values. The S-plot thus compares two samples (for example, with n=3 measurements, minimum). For example, AMRT pairs and/or CCS measurements of components from reference and test ampholyte compositions can be plotted using S-plots. In an S-plot, the covariance, or magnitude of change, is plotted on the x-axis, while the correlation, i.e. the consistency of the change is plotted on the y-axis. The farther from the origin the x-axis the marker is located, the greater its contribution to the variance between the groups, while markers farther along the y axis represent a higher reliability of the analytical result. In an exemplary S-plot, covariance of AMRT pairs from the at least one test ampholyte composition and the reference ampholyte are plotted.

Every point on an S-plot is a specific m/z, with an associated RT and CCS value. Markers are plotted by consistency across replicates vs magnitude of the change. The farther away from the origin along the x-axis, the greater difference there is in intensity (or relative concentration) between the samples. The differences between groups can be from markers that are only present in one group, or from markers that have a large change in intensity between groups. The farther away from the origin on the y-axis, the more reliable the analytical results are across the triplicate measurements. The S-plot can be used to identify which features are most different between lots, and those markers can be used to generate a screening library to characterize ampholyte lots.

In some embodiments, the methods of identifying at least one marker to determine the suitability of an ampholyte composition comprise (i) determining Accurate Mass/Retention Time (AMRT) measurements for a plurality of components of the at least one test ampholyte composition and the reference ampholyte composition; (ii) plotting covariance of the AMRT measurements for the plurality of components from the at least one test and reference ampholyte compositions using an S-plot; and (iii) selecting at least one component that is different between the at least one test ampholyte composition and the reference ampholyte compositions, wherein the difference comprises a covariance that is less than 0 in the S-plot; thereby identifying at least one marker for characterizing the suitability of the at least one test ampholyte composition. When covariance is less than 0 on the S-Plot, the AMRT paired values are negatively correlated between the reference and test ampholyte compositions. Accordingly, the at least one marker is selected based on differences between the reference and test ampholyte compositions, and differences in the presence and/or level of the at least one marker between reference and test ampholyte compositions determines the suitability of the test ampholyte composition.

In some embodiments, for example those embodiments where the at least one marker is a marker of differences between the reference and test ampholyte composition, the at least one component selected as a marker comprises a covariance in the S-plot that is less than the covariance of at least 20%, at least 30%, at least 40%, at least 50%, at least 60%, at least 70%, or at least 80% of the plurality of components in the S-plot.

In some embodiments, the difference in the level of the at least one marker comprises a difference in level of at least 10%, at least 20%, at least 30%, at least 40%, at least 50%, at least 60%, at least 70%, at least 80%, or at least 90% relative to a normalized level of the at least one marker. For example, the reference ampholyte composition comprises a normalized level of the at least one marker that is 100%, and the test ampholyte composition comprises a normalized level of the at least one marker that is 30%. Markers can be characterized by mass to charge ratio (m/z), and levels of markers determined by relative intensities normalized to maximum relative intensities as described herein.

In some embodiments, the methods of identifying at least one marker to determine the suitability of an ampholyte composition comprise (i) determining Accurate Mass/Retention Time (AMRT) measurements for a plurality of components of the at least one test ampholyte composition and the reference ampholyte composition; (ii) plotting covariance of the AMRT measurements for the plurality of components from the at least one test and reference ampholyte compositions using an S-plot; and (iii) selecting at least one component that is similar between the at least one test ampholyte composition and the reference ampholyte compositions, wherein the similarity comprises a covariance that is greater than 0 in the S-plot; thereby identifying at least one marker for characterizing the suitability of the at least one test ampholyte composition. When covariance is greater than 0 on the S-Plot, the AMRT paired values are positively correlated between the reference and test ampholyte compositions. Accordingly, the at least one marker is selected based on similarities between the reference and test ampholyte compositions, and similarities in the presence and/or level of the at least one marker between reference and test ampholyte compositions determines the suitability of the test ampholyte composition.

In some embodiments, for example those embodiments where the at least one marker is a marker of similarities between the reference and test ampholyte compositions, the at least one component selected as a marker comprises a covariance in the S-plot that is greater than the covariance of at least 40%, at least 50%, at least 60%, at least 70%, at least 80%, at least 90%, at least 95%, or at least 99% of the plurality of components in the S-plot.

In some embodiments, the at least one test ampholyte composition has suitable activity if the level of the at least one marker in the at least one test ampholyte composition and the reference ampholyte composition is similar. In some embodiments, the similarity in the level of the at least one marker comprises a level that is at least 20%, at least 30%, at least 40%, at least 50%, at least 60%, at least 70%, at least 80%, at least 90%, at least 95% or at least 99% similar relative to a normalized level of the at least one marker. For example, the reference ampholyte composition comprises a normalized level of the at least one marker that is 100%, and the test ampholyte composition comprises a normalized level of the at least one marker that is at least 90%. As a further example, the reference ampholyte composition comprises a normalized level of the at least one marker that is 100%, and the test ampholyte composition comprises a normalized level of the at least one marker that is at least 80%. Markers can be characterized by mass to charge ratio (m/z), and levels of markers determined by relative intensities normalized to maximum relative intensities as described herein.

The disclosure provides methods of determining the degree of similarity or difference of at least one marker between at least one test and a reference ampholyte composition. In some embodiments, the methods comprise (i) determining a LC-MS mass spectrum of the at least one marker in the at least one test ampholyte composition and the reference ampholyte composition, (ii) determining the relative intensity of a base peak for the at least one marker in the mass spectrums of the at least one test ampholyte composition and the reference ampholyte composition, (iv) normalizing the relative intensity of the base peak of the at least one marker to a maximum relative intensity of the base peak measured from the at least one test ampholyte composition or the reference ampholyte composition, and (iv) comparing the relative intensities of the normalized relative intensities of the base peak of the at least one marker in the at least one test and reference ampholyte compositions.

In some embodiments, the at least one marker comprises a plurality of markers. In some embodiments, the at least one marker comprises at least 2, 3, 4, 5, 10, 15, 20, 25, 30, 35, 40, 45, 50, 75 or 100 markers with different m/z.

In some embodiments, the at least one marker comprises 1, 2, 3, 4, 5, 6, 7, 8, 9, 10, 11, 12, 13, 14, 15 or 16 markers with different m/z.

In some embodiments, the at least one marker comprises 16 markers with different m/z. In some embodiments, the 16 markers comprise markers with an m/z of 280, an m/z of 319, an m/z of 329, an m/z of 347, an m/z of 373, an m/z of 375, an m/z of 376, an m/z of 431, an m/z of 504, an m/z of 506, an m/z of 508, an m/z of 520, an m/z of 534, an m/z of 562, an m/z of 906 and an m/z of 980.

Suitable pluralities of markers of different m/z that can be used to characterize test ampholyte compositions may be determined de novo relative to a reference ampholyte composition using the methods described herein. For example, by characterizing the reference and test ampholyte compositions via LC-MS, plotting AMRT pairs via S-Plot, and selecting at least one or a plurality of markers based on covariance.

Alternatively, or in addition, test ampholyte compositions may be characterized using the methods described herein via comparison to a pre-determined library of markers that were previously determined using the method described herein. For example, relative intensities of at least one or a plurality of markers of the test ampholyte composition can be determined via LC-MS, and compared to a pre-determined reference or standard library of markers.

The present description sets forth numerous exemplary configurations, methods, parameters, and the like. It should be recognized, however, that such description is not intended as a limitation on the scope of the present disclosure, but is instead provided as a description of exemplary embodiments.

EXAMPLES

Example 1: Imaging Capillary Isoelectric Focusing (iCIEF) Protocol to Determine Protein Charge Variant Levels and/or Identity of Protein Products iCIEF is used for laboratory testing of drug substances, formulated drug substances, drug products, and in-process materials for which written specifications have been established. When used for release testing against specifications, the standard operating procedures (SOP) for iCIEF must be followed and any deviation must be addressed. What follows is an exemplary iCIEF SOP protocol whose outcome is affected by lot-to-lot variation in the ampholyte lot used in the SOP protocol.

Definitions iCIEF— Imaged capillary isoelectric focusing.

pI— Isoelectric point, pH of a molecule where the net charge is zero.

Region 1 (Acidic)— Group of peaks that are relatively acidic comparing to the largest peak of an iCIEF electropherogram.

Region 2 (Neutral)— The principal peak/peaks corresponding to the largest protein peak/peaks.

Region 3 (Basic)— Group of peaks that are relatively basic comparing to the largest peak of iCIEF electropherogram.

Ampholytes— Compounds containing both positive and negative charges that behave as zwitterions at and near their pI values. The ampholytes assist in the formation of the pH gradient during focusing.

Transfer Time Measurement— An experiment performed to ensure proper sample injection. The measurement is performed when starting up the iCE3 instrument or installing a new cartridge.

Premixed Mode— Protein samples are premixed with carrier pharmalytes, additives and pI markers.

Materials
- Safe-Lock Eppendorf Tubes, 1.5 mL (VWR, cat. #21008-959) or similar tube of the same materials of construction
- cIEF Cartridge FC-Coated (ProteinSimple, PN 101701)
- 10 mL amber vials, 22×75, with caps (thin septa) (ProteinSimple, PN 045-139)
- Polypropylene vial with 300 µL molded insert (ProteinSimple, PN 045-133)
- Septa pack iCE3 (300 µL caps) (ProteinSimple, PN 045-134)
- Electrolyte Pipette (ProteinSimple, PN 101788) or similar pipette of the same materials of construction
- Microinjector Transfer Capillary, Coated (ProteinSimple, PN 102694)
- 5 mL Microtube, Natural (Argos Technologies, cat #T2076) or similar tube of the same materials of construction
- Amicon Ultra-0.5 Centrifugal Filter Unit with Ultracel-10 membrane (Millipore, cat #UFC501096)

Chemicals
- Water, purified by Milli-Q system or purchased such as HPLC Grade Water (VWR, cat. #JT4218-3) or Water for Injection (WFI), (APP Pharmaceuticals, cat. #918510)
- Appropriate Antibody Reference Standard (current standard lot)
- Urea (Sigma-Aldrich, BioXtra cat #U0631)
- 3-10 Pharmalytes (VWR cat. #17-0456-01 or Sigma cat. #P1522-25 ML) Store at 2-8° C.
- 0.5% Methyl Cellulose (MC) Solution (ProteinSimple, PN 102505)
- 1% Methyl Cellulose (MC) Solution (ProteinSimple, PN 101876)
- Electrolyte Kit (ProteinSimple, PN 102506):
  - 100 mL 0.08 M H3PO4
  - 100 mL 0.1 M NaOH
- pI Marker pI 5.12 (ProteinSimple, PN 102224)
- pI Marker pI 9.50 (ProteinSimple, PN 101996)

Equipment
- Microcentrifuge for test preparation
- ProteinSimple iCE3 Charge Variant Analyzer
- VWR Single-Channel Pipettors (VWR #89130-554, 556, 560, 562, 566) or pipettes with similar ranges
- Sterile Pipette Tips (VWR) or tips matching pipettes used
- Positive displacement pipettes (Rainin #MR-10, MR-100, MR-250, MR-1000)
- Rainin positive pipette tips (Rainin #C-10, C-100, C-250, C-1000)
- Eppendorf Repeater Plus Pipettor (VWR, cat #21516-002)
- Eppendorf Combitips Pipette Tips (VWR, cat #21516-138)
- Analytical Balance Reagent Solutions Volumes of reagent solutions can be adjusted as needed.

8M Urea Solution: to prepare 8M Urea solution, weigh out 2.4 g of Urea in a 5 mL conical tube. Slowly add water to approximately 4 mL mark Agitate mixture until Urea is dissolved. Bring the solution to the final volume of 5 mL with water. Mix well. Prepare fresh daily.

Master Mix: the following is a single preparation that should be scaled as needed. For the generic iCIEF method, the pI 5.12 marker and pI 9.50 marker are recommended as acidic and basic markers. Master mix should be mixed well, and prepared fresh daily.

TABLE 1

Master Mix

| Component | Amount |
| --- | --- |
| 8M Urea Solution | 50 µL |
| 3-10 Pharmalytes | 8 µL |
| 1% Methyl Cellulose (MC) Solution | 70 µL |
| Water | 30 µL |
| pI Marker (acidic) | 1 µL |
| pI Marker (basic) | 1 µL |

Procedure

A standard start up procedure to initiate the iCE3 can be used.

Reference Standard Preparation: Any current reference standard may be used to demonstrate system suitability. The appropriate reference sample is diluted to 2 mg/mL using water. Standards are mixed by gentle inversion and the tubes spun approximately 15 seconds in a microcentrifuge.

In a separate tube, combine 40 µL of the 2 mg/mL reference standard or test article preparation with 160 µL of Master Mix. In order for the required system suitability injections, at least 2 vials must be prepared. This preparation may be scaled accordingly. Mix by gentle inversion and spin approximately 15 seconds to drive the contents to the bottom of the tube.

In-process Sample Preparation: Dilute the in-process sample to 2 mg/mL using water. Mix by gentle inversion. Assemble a centrifugal filtration device by placing filter in clean microcentrifuge tube. Pre-wet the membrane of the filter by pipetting 400 µL water into filter, ensuring that the entire membrane has been covered. Remove water from the filter by pipetting and dispose of the water in waste container. Load 200 µL of the diluted 2 mg/mL in-process sample into pre-wet filter. Close the centrifugal filtration device by capping the microcentrifuge tube in the attached filter. Centrifuge the device at 14,000 relative centrifugal force (rcf) for 15 minutes.

Remove the device from the centrifuge. Remove the filter from the device and invert it into a clean microcentrifuge tube. Discard the microcentrifuge tube containing the removed buffer. Once the filter is placed in a clean microcentrifuge tube, it will not be able to be capped. Place the uncapped device with inverted filter into the centrifuge and spin for 2 minutes at 1,000 rcf. Following centrifugation, the concentrated protein will be in microcentrifuge tube. Discard the filter.

Reconstitute the concentrated protein in 180 µL water. Mix by gentle inversion and spin approximately 15 seconds to drive the contents to the bottom of the tube.

Mix 40 µL of the filtered sample with 160 µL Master Mix. Mix by gentle inversion and spin approximately 15 seconds to drive the contents to the bottom of the tube.

Drug Substance, Formulated Drug Substance and/or Drug Product Preparation: if sample concentration is less than 20 mg/mL, the buffer exchange procedure described above for the in-process sample should be followed instead of the protocol below for drug substance, formulated drug substance or drug product preparation.

If the drug substance, formulated drug substance or drug product is an antibody, it should not be vortexed at any time during preparation.

Dilute the test article (the drug substance, formulated drug substance or drug product) to 2 mg/mL using water. Mix by gentle inversion and spin tubes approximately 15 seconds in a microcentrifuge. In a separate tube, combine 40 µL of the 2 mg/mL test article preparation with 160 µL of Master Mix. Mix by gentle inversion and spin approximately 15 seconds to drive the contents to the bottom of the tube.

Blank Preparation: Mix 40 µL water with 160 µL Master Mix. Mix by gentle inversion and spin approximately 15 seconds to drive the contents to the bottom of the tube.

Sample loading using iCE3 Instrumentation: use the iCE3 premixed mode. Transfer 150 µL of the supernatant of samples (Reference Standard/Reference Solution, test article, and blank preparation) prepared as described above into a polypropylene vial with 300 µL molded insert. Ensure there are no air bubbles in the bottom of the vials.

Place the sample vials into the Alcott 720 autosampler. Fill a 10 mL amber vial with approximately 8 mL of 0.5% Methyl Cellulose (MC), and place in "D" position in the autosampler. Use fresh MC solution daily to prevent microbial growth. Insert the water line into a fresh bottle of Milli-Q water, and place above the instrument. Place the waste line into a designated waste container.

Batch setup and initiation (iCE3): open the CFR Software. Click Batch/Data and select Development. The "Batch File Control" window will appear. Create a batch file using one of the following options:
(1) to create a new batch file, enter a Batch File Name and select a folder to save the batch in. Select the # of Injection Runs and click New File.
(2) to start a new batch file using a previously saved batch file as a template, find the desired file in the left pane of the "Batch File Control" window. Click Open File. Click the Save As button, enter a new file name and click OK.

In a batch, the initial injection should be a blank. Test articles must be bracketed by at least five injections of an appropriate product reference standard. Three reference standard injections before test article injection and two following are recommended for a total of five reference standard injections.

Occasionally missed injections or random spikes that interfere with the protein profile may occur resulting in atypical electropherograms (in terms of intensity, number, and pattern of peaks). Re-injections of blank, reference standard and test article can be made within 24 hours of the initial injection using at least five reference standard injections as brackets, provided the reference standard used is appropriate for the associated sample injections.

Set-up the Batch Focus Period Settings: enter a unique and descriptive file name for each injection. For the Sample ID, enter the Reference Standard/Reference Solution designation, LIMS #, or other sample identifier. Number vials sequentially. Focus Period 1 (Pre-focusing) uses the following settings: 1 minute at 1500 V. Focus Period 2 (Focusing) uses the following settings: 7 minutes at 3000 V. The Wash duration is 90 seconds, and the Transfer Time Delay is 0.00 minutes.

Set the Autosampler Parameters:
Temperature Control: Yes; set to 10° C.
Buffer Injection Duration: Default value.
Sample Injection Duration: Default value.
Load Duration: 6 seconds.
Vial Type: 2 mL with 300 µL insert.
Needle Depth: 48 mm.

Sample and Buffer Injection Durations are determined during the Transfer Time Measurement (system check for Startup/Cartridge Installation) and are based on the length of time for the plateau to appear. At least 10 seconds longer than the length of the time for the plateau is recommended.

Enter the following information under Sample Conditions:
Carrier Ampholytes: 4% 3-10 Pharmalytes
Additives: 2 M Urea, 0.35% MC
Low pI Marker: pI value of acidic marker in the Master Mix (5.12)
High pI Marker: pI value of basic marker in Master Mix (9.50)
Concentration [µg/µL]: 0.40
Choose Sample Type (optional)

Note that for Concentration, the concentration of a blank is 0. Final concentrations of in-process samples may vary depending on the dilution factor used.

Data Conversion

Data conversion can be carried out using iCE CFR Software. CFR Software can be used to generate electropherograms and set pI markres for the blank, reference standard and test sample electropherograms. CFR Software can also be used to convert data to other formats, such as Empower, for additional analysis.

System Suitability

Both acidic (low) and basic (high) pI markers must be present in the electropherograms of the blank, reference standard and test article injections. Replicate reference standard injections must be similar in profile (i.e. in terms of intensity, number, and pattern of peaks). Region 1 and Region 2 of at least five replicate reference standard injections must each have an average % area result that meet the product specification with a % RSD≤5%.

Assay Validity Check

The test article profile must be qualitatively similar to example electropherogram from the product specific job aid in terms of intensity, number, and pattern of peaks. There should be no peaks in the blank injection protein region of interest as integrated in the appropriate product specific job aid.

Protein Charge Variant Analysis

Results are reported to one decimal place. For the reference standard, the average replicate % area of Regions 1, 2 and 3 from all injections is reported. The % RSD between all replicate injections of Regions 1, 2 and 3, and the average pI value of Region 2, for information only, is also reported. For the test article (sometimes referred to as test sample) data as specified in the appropriate product specification or protocol is reported. If there is no protocol available, the % area of Regions 1, 2 and 3 is reported. The average pI value of Region 2 is reported, for information only.

Example 2: Variation in Ampholyte Lot Causes Electropherogram Variance

Ampholytes are a critical reagent for iCIEF assays. However, different lots of ampholytes give different electropherograms, even when analyzing the same reference protein, leading to quality control testing failure (compare FIGS. 1A and 1B).

Reference Protein 1 was analyzed using iCIEF as described for Example 1 above, using ampholyte lot 1 (the current standard) and various test ampholyte lots. Table 1 below summarizes GE ampholyte lots tested throughout the course of this analysis.

TABLE 1

Figure 1B:
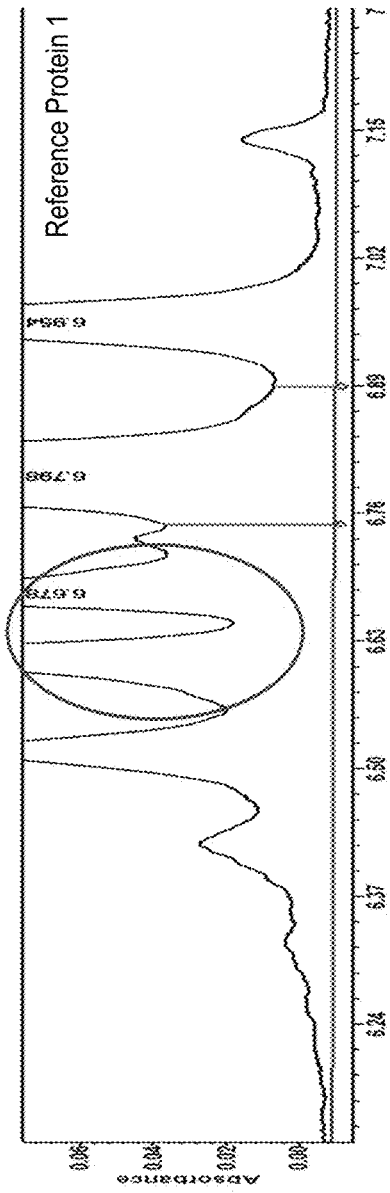
Figure 2:
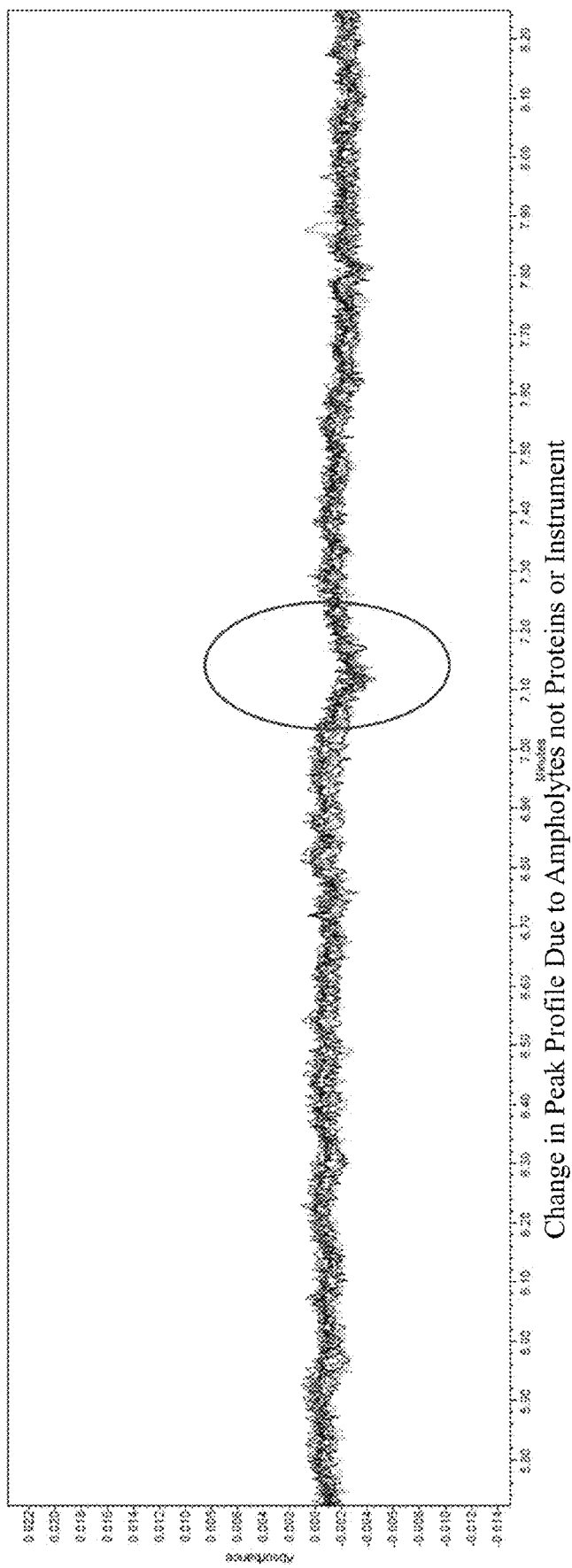
FIG. 2 is a plot showing baseline interference based on the ampholyte gradient used in iCIEF. ICIEF was run without the Reference Protein. Increasing ampholyte concentration led to a drop in baseline dip. This change in peak profile was due to ampholytes, and not proteins or the instrument.
Figures 4A, 4B:
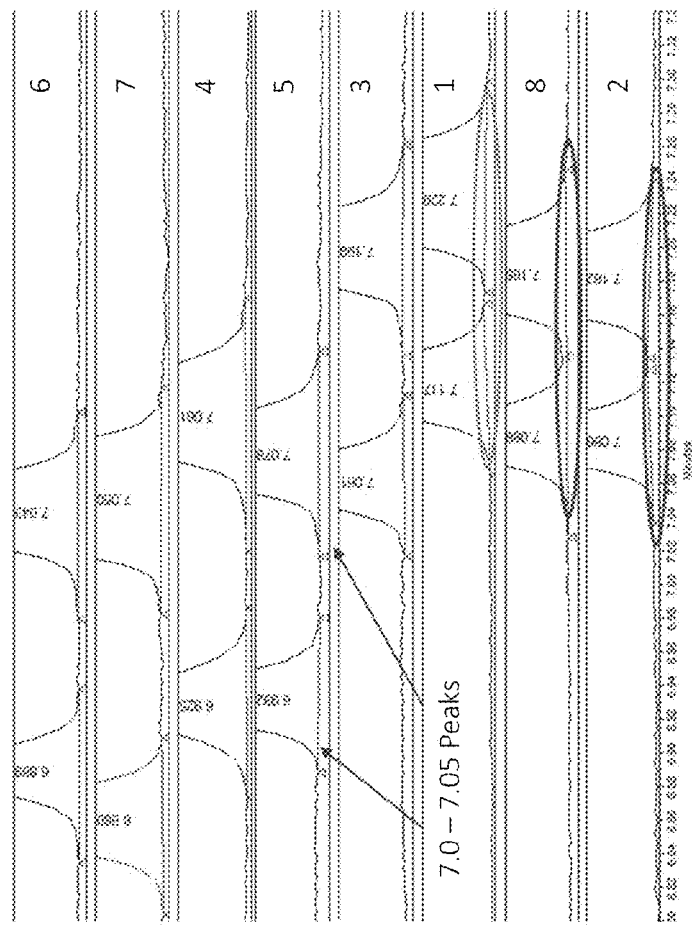
FIGS. 4A-4B are a series of electropherograms (FIG. 4A) and a table (FIG. 4B) showing resolution variance within ampholyte lots. Lots 7 and 2 are the most suitable candidates for statistical analysis for a lot most similar to lot 1.
Figures 10A, 10B:
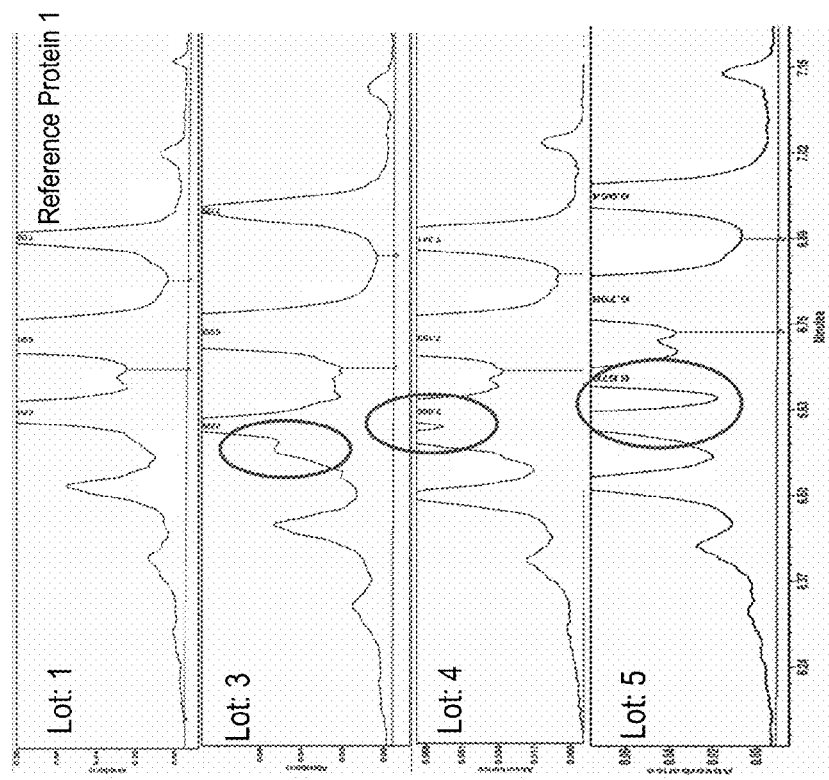
FIG. 10A is a table showing a library of ampholyte components characterized by m/z value (the mass to charge ratio) and their normalized relative intensities in ampholyte Lot numbers 1 (the current lot used in standard operating procedure, or SOP lot), 2, 3, 4 and 5. Relative intensities were normalized to the highest relative intensity across all ampholyte lots. Marker response values were assessed and compared in excel.
FIG. 10B shows iCIEF electropherograms analyzing Reference Protein 1 product using 5 different ampholyte lots. From top to bottom: lot 1 (SOP), lot 3, lot 4 and lot 5. Differences in the iCIEF profiles are circled.

GE Healthcare Pharmalytes pH 3-10 Lots
GE Lots Analyzed 1 (current standard)
2
3
4
5 iCIEF electropherograms of Reference Protein 1 generated under otherwise identical conditions, but with different ampholyte lots, displayed substantial differences in profile (compare FIG. 1A with FIG. 1B, compare electropherograms in FIG. 4A or FIG. 10B, for example).

Figure 3:
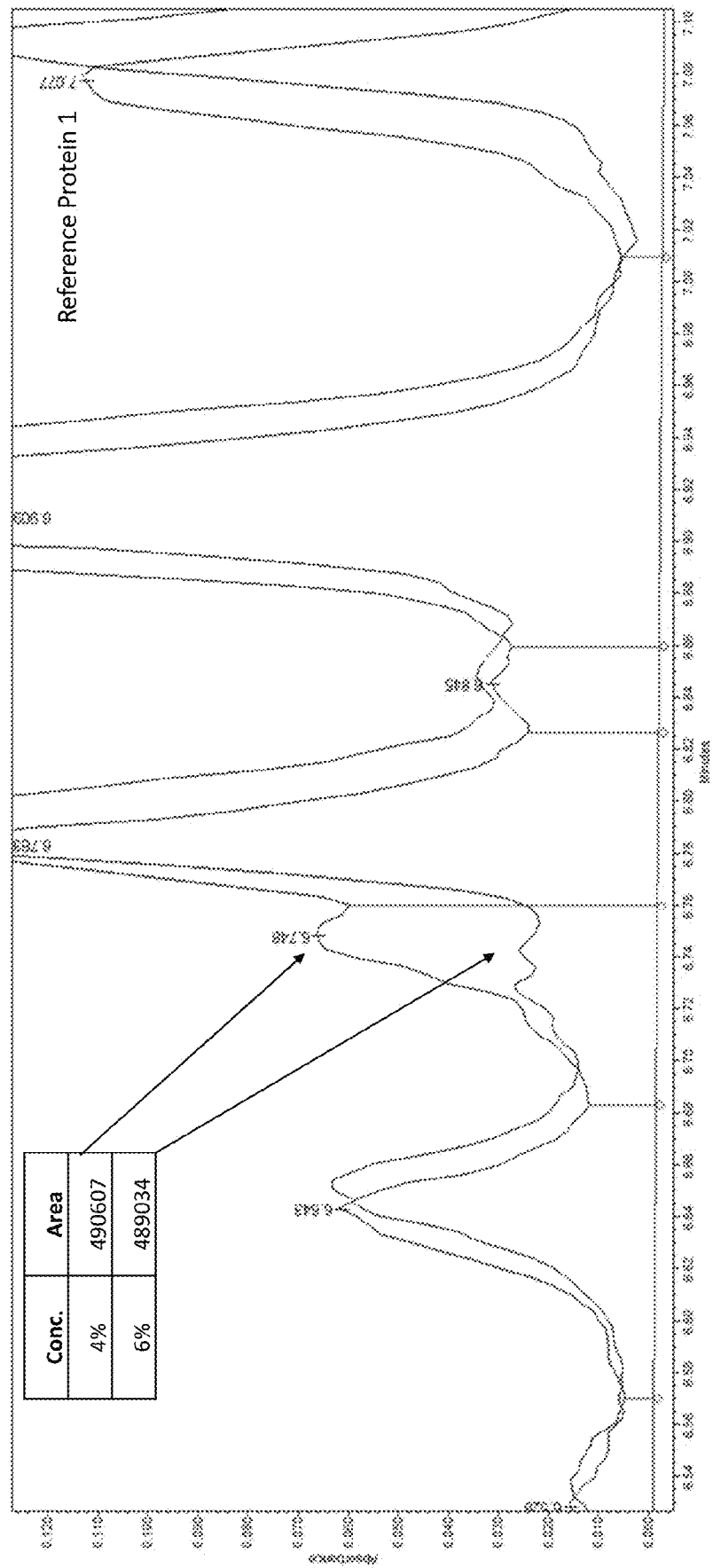
FIG. 3 is an electropherogram showing that pharmalyte (ampholyte) concentration leads to changes in region area. A 2% change in pharmalyte concentration caused a 1% decrease in the area of Region 1.

Varying pharmalyte concentration in iCIEF analysis showed that as little as a 2% change in ampholyte concentration could cause changes in electropherograms. For example, changing the ampholyte concentration from 4% to 6% led to a 1% decrease in the area of Region 1 for Reference Protein 1 (FIG. 3).

Differences in ampholyte lot also affected the resolution of peaks in the iCIEF electropherograms. As shown in FIGS. 5A-5C, the resolution of each ampholyte was calculated for pI between 7.0 and 7.05. As shown in FIGS. 4A-4B, different ampholyte lots show different resolution of peaks between 7.0 and 7.05.

Example 3: Characterization of Ampholyte Lot by LC-MS and Marker Library Creation Traditionally, ampholyte lots are indirectly evaluated by assessing iCIEF assay performance. The inventors have developed methods of direct ampholyte lot characterization. These methods analyze the ampholytes themselves using LC-MS, rather than assaying the ability of ampholyte lots to generate electropherograms of a known protein reference. This method characterizes the chemical composition of the ampholytes themselves by UPLC IMS-Q-ToF-MS and correlates it to iCIEF assay performance using the known reference protein.

GE ampholyte lot 1 was used to establish the criteria in the standard operating procedures (SOP). However, a replacement lot is needed. Lot-to-lot variation has been observed across GE ampholyte lots, and these differences have resulted in dissimilar electropherograms during repeated analyses of the same sample, leading to QC test failures. This can be seen in Example 2.

Thus, an ampholyte characterization method has been developed using UPLC IMS-Q-ToF-MS to evaluate candidate lots. The objective is to chemically characterize ampholyte lots and monitor the components that are varying between them. This offers an ampholyte characterization methods for future GE candidate lots and serves as a workflow that can be applied to other vendors. Even without vendor provided ampholyte composition, this method allows for comparing a candidate lot to a current lot using multi-variate statistical analysis to assess the differences.

As a further advantage, using these methods, no protein reference standard is consumed, and there is a 70:1 sample savings, or decrease in sample consumed.

Figure 7:
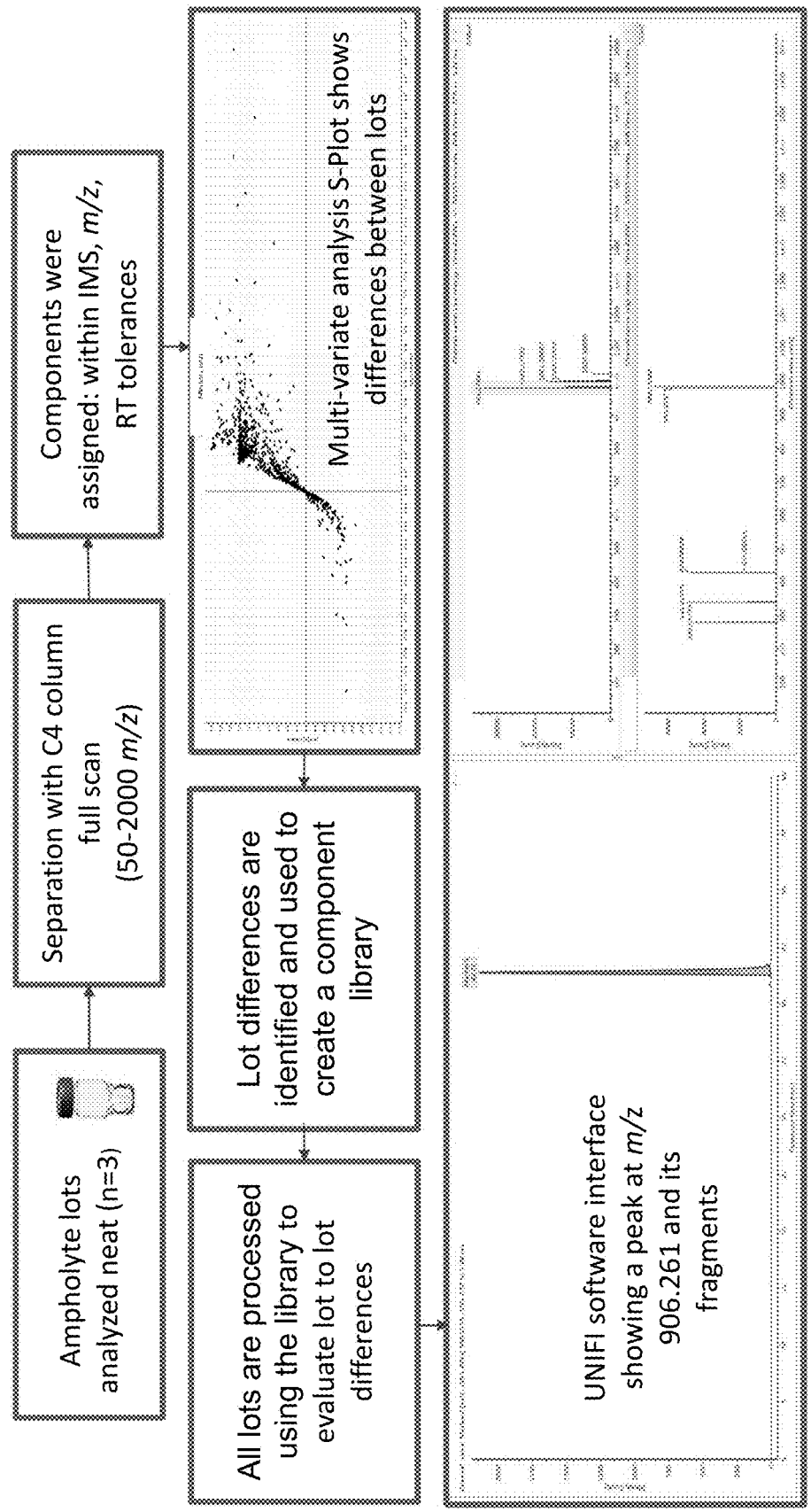
FIG. 7 is a diagram showing an ampholyte LC-MS analysis workflow.

An outline of ampholyte testing methods is shown in FIG. 7. In brief, ampholyte lots are analyzed neat in triplicate. Ampholyte lots are separated using Waters VION IMS QTof Ion Mobility Quadrupole Time-of-flight Mass Spectrometry (LC-IMS-Q-TOF-MS) with a C4 column and a full scan, which identifies ampholyte lot components with a mass to charge ratio (m/z) between 50 and 2000, although this range can vary. Components were assigned within ion mobility spectrometry (IMS), m/z and retention time (RT) tolerances. Differences in components identified by LC-MS were analyzed via multi-variate analysis and plotted using Waters S-Plots. The multi-variate analysis identified differences between ampholyte lots that was used to create a component library which can be used to evaluate lot-to-lot differences predict which lots will behave similarly to the standard ampholyte lot in an iCIEF assay with a reference protein.

FIG. 8A shows ampholyte lots that were analyzed by LC-MS to create the component library.

FIG. 8B shows an example Waters S-Plot of ampholyte LC-MS data. The Waters S-Plot shows Accurate Mass/Retention Time (AMRT) dissimilarities between two lots of ampholytes. AMRT pairs are plotted by covariance. The magnitude of change is shown on the x-axis, and correlation, or the consistency of the change is shown on the y-axis. I.e., the further along the x-axis a marker component is located, the greater the contribution of that marker to the variance between ampholyte lots, and the greater the difference in concentrations of that marker between lots. The further along the y-axis a marker component is located, the greater the consistency of the result between replicates. Differences between ampholytes could be due to components which are present or not present in one or more ampholyte lots, and/or changes in concentration of select markers between lots.

UPLC IMS-Q-ToF-MS Procedure:

Separation was carried out on a Waters Acquity UPLC H-Class system with degasser, chiller, quaternary pump, and autosampler. A Waters BEHTM C4 2.1×100 mm analytical column, with a 1.7 µm particle size, was operated at a flow rate of 0.2 mL/min. A 10 µL aliquot was used for sample injection. The mobile phase consisted of 0.1% formic acid in water (A) and 0.1% formic acid in acetonitrile (B). The gradient starts with 95% A and 5% B kept for 5 minutes followed by a linear ramp to 95% B after 35 minutes. This condition was maintained for 5 minutes before switching back to 95% A at 50 minutes. The column was kept at this condition for another 10 minutes for column re-equilibration; total run time is 60 minutes.

A Waters Vion IMS-Q-ToF-MS was used under positive electrospray ionization (+ESI) in Accurate Mass Screening on MSe data mode. The mass spectrometer had the following settings: capillary voltage (2.00 kV), source temperature (150° C.), desolvation temperature (200° C.), cone gas (25 L/h) and desolvation gas (800 L/h). Data collection and analyses were performed with UNIFI' software version 1.9.4.0.

Five ampholyte lots (−1, −2, −3, −4, and −5) were evaluated, and 500 µL of each lot was spiked with 25 µL of 1 µg mL-1 of $^{13}C_6$-carbamazepine, which was selected as an internal standard due to its mid-run elution and high ionization efficiency. The response of the internal standard was used to normalize the response values for each m/z marker to account for instrument drift. Additionally, the change in retention time (RT), collisional cross section (CCS), and m/z of the internal standard over the course of the run was used to set the tolerances on the parameters for marker assignment. Each ampholyte sample was injected neat (n=3) from the same vial. Starting mobile phase composition blanks were also analyzed between each lot.

Figure 10C:
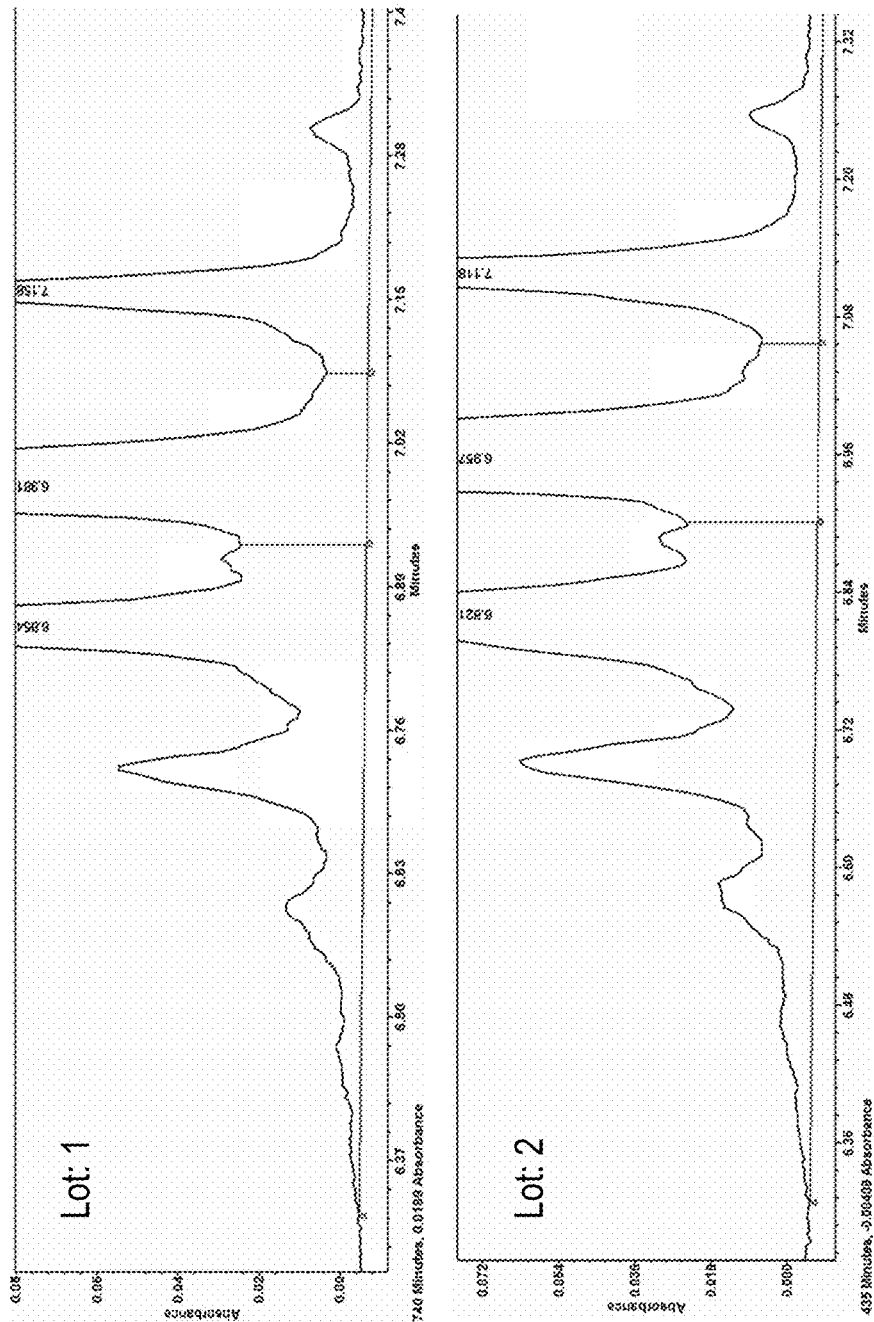
FIG. 10C shows iCIEF electropherograms analyzing Reference Protein 1 product using ampholyte lot 1 (top, SOP) and 2 (bottom). Lot 2 was run after the LC-MS results were analyzed and it was predicted to be the most similar lot to lot 1 (see FIG. 10A).

Data processing began with filtering and statistical analysis. A principal component analysis (PCA) allows for reducing large sets of multivariate data into uncorrelated variables known as principal components. PCA is limited in that no information about individual sample groups can be ascertained from the plot, but the data can be further mined using an orthogonal projection to latent structures—discrimination analysis (OPLS-DA). This statistical analysis allows for identifying specific features (i.e. ampholyte species) that contribute to the overall differences observed between two groups and can be viewed as an S-plot. An S-plot compares two samples (n=3 measurements, minimum); every point on an S-plot is a specific m/z, with an associated RT and CCS value. Markers are plotted by consistency across replicates vs magnitude of the change. The farther away from the origin along the x-axis, the greater difference there is in intensity (or relative concentration) between the samples. The differences between groups can be from markers that are only present in one group, or from markers that have a large change in intensity between groups. The farther away from the origin on the y-axis, the more reliable the analytical results are across the triplicate measurements. The S-plot was used to identify which features are most different between lots, and those markers were added to a screening library. Markers that were selected must have been present in all 3 measurements of the ampholyte sample and must not have been present in the blanks. This library was then used to evaluate the presence or absence of specific markers to each lots, as well as presence at a specific intensity. Markers that were suspected to have a greater impact on assay performance were further investigated by elucidating the structure and performing a database search for identification. Results:

FIGS. 10B-10C show the variation in iCIEF profiles generated using lots 1, 3, 4 and 5. Testing by iCIEF found that lot 5 performed the most different when compared to lot 1 (FIGS. 10B-10C). In FIG. 10B, electropherograms grow progressively more dissimilar to lot 1, proceeding down from lot 1. The electropherogram generated using lot 2 (FIG. 10C), was the most similar to that generated by lot 1. From the marker library in FIG. 10A, lot 2 was predicted to have the most similarity in ampholyte components to lot 1, the current standard ampholyte lot. As can be seen from FIG. 10C, when lot 2 was used to generate an iCIEF profile of Reference Protein 1, this profile was more similar to the lot 1 Reference Protein 1 profile than any of the iCIEF profiles generated by lots 3, 4 or 5 (FIG. 10B). Therefore, the ampholyte component library can be used to directly identify ampholyte lots that produce iCIEF profiles similar to the standard lot, lot 1.

Figure 9A:
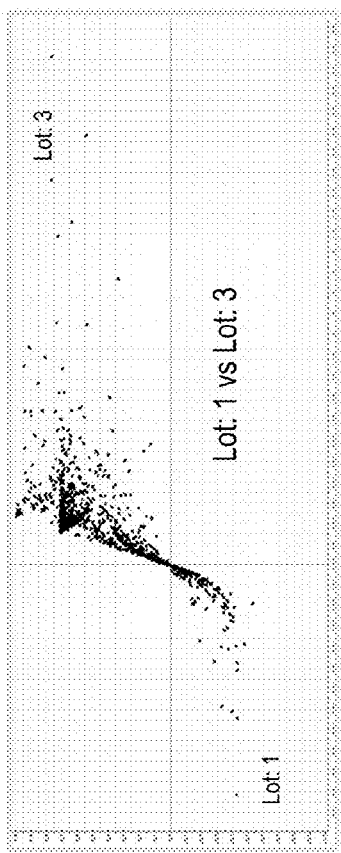
FIGS. 9A-9C are Waters S-Plots comparing ampholyte lots characterized using Waters VION IMS QTof Ion Mobility Quadrupole Time-of-flight Mass Spectrometry (LC-IMS-Q-TOF-MS).
Figure 9B:
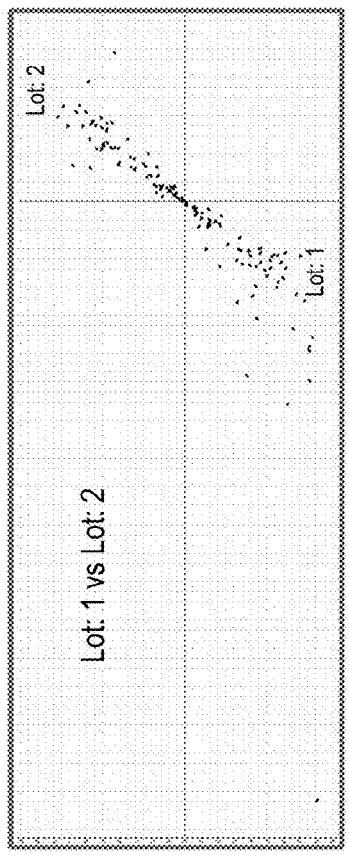
Figure 9C:
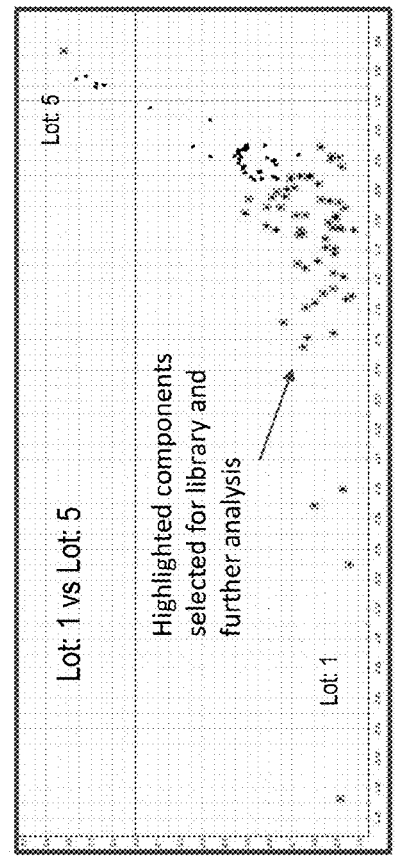

FIG. 9A-9C show Waters S-Plots comparing three different ampholyte lots to the current standard lot, lot 1. The S-plot of 1 vs 5 showed that there were many features in lot 1 that are absent or lower intensity in lot 5 (FIG. 9C). The markers that varied the most were added to the library (see FIG. 10A) used to characterize other ampholyte lots. The S-plot of 1 vs 2 in FIG. 9A showed agreement between the two lots. This finding was supported by the iCIEF results, which found that of all the GE lots tested, 2 gave the most similar result to 1. No markers were selected from this S-plot.

Figure 11B:
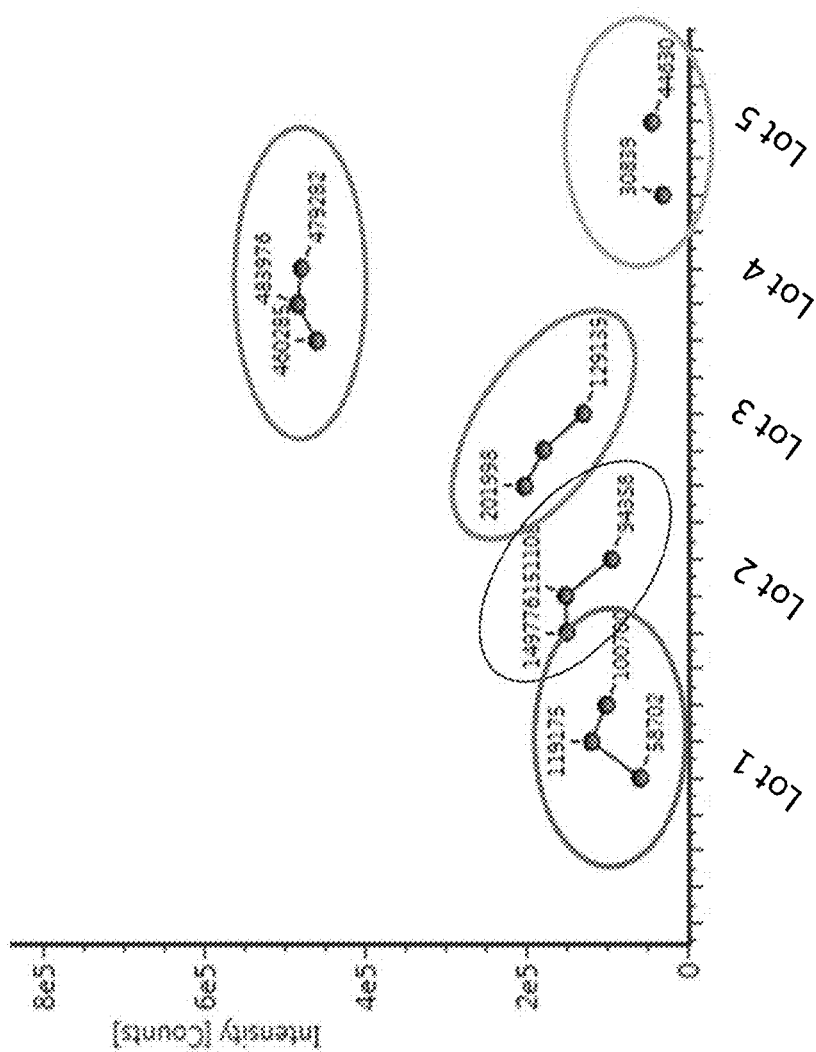
FIG. 11B is a trend plot showing markers in three replicates of the indicated ampholyte lot (x-axis indicates lot and replicate), versus marker intensity (y-axis, counts). Markers were considered relevant if they were identified in all three replicates of the current lot and were not detected in a blank.

The boxed points in FIG. 10C indicate components that were selected for a library of components used to characterize ampholyte lots. Markers that were identified from the S-plot were manually evaluated to ensure they were present in all three measurements of the lot they were detected in and that they were unique to ampholytes and not present in the blank (FIG. 11B).

Figure 11A:
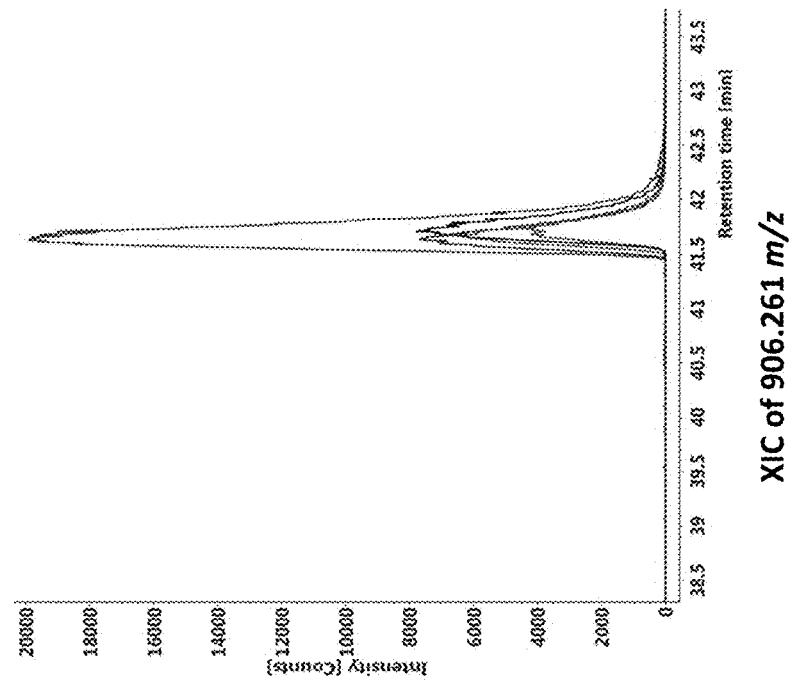
FIG. 11A is a plot showing the ion mobility filtered extracted ion chromatogram (XIC) of marker m/z 906.261 from each of the lots of ampholytes indicated. The response of the XIC is used for lot-to-lot comparison.
Figure 12:
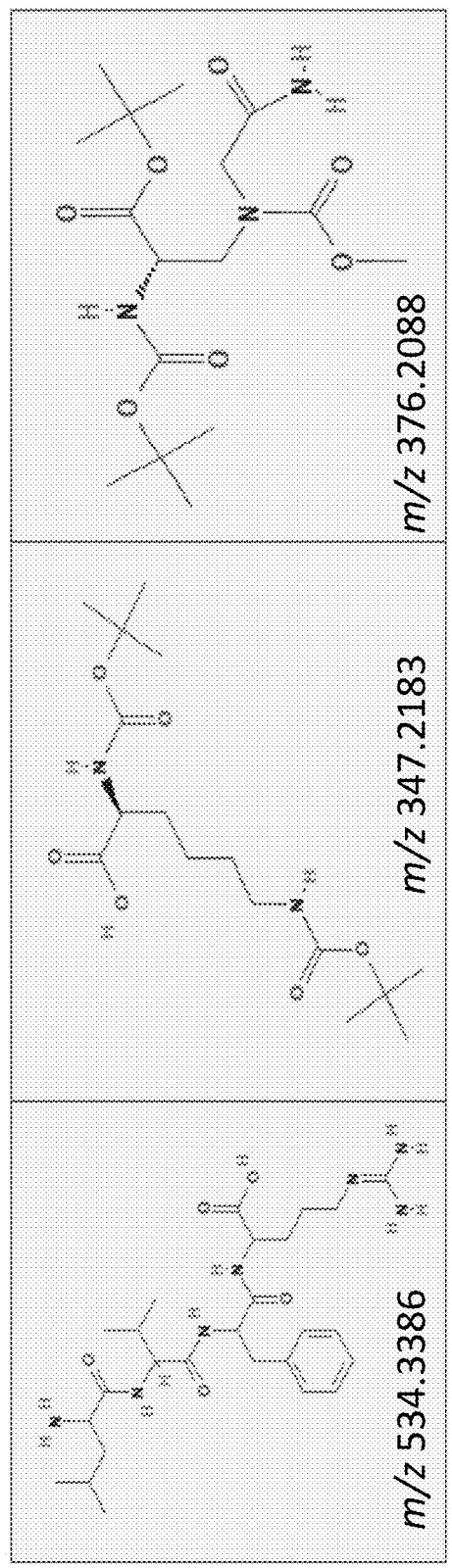
FIG. 12 shows the structures of three markers from the library used to characterize ampholyte lots. Structures correspond to markers with the m/z values at bottom. These are commercially available elucidation results.
Figure 13:
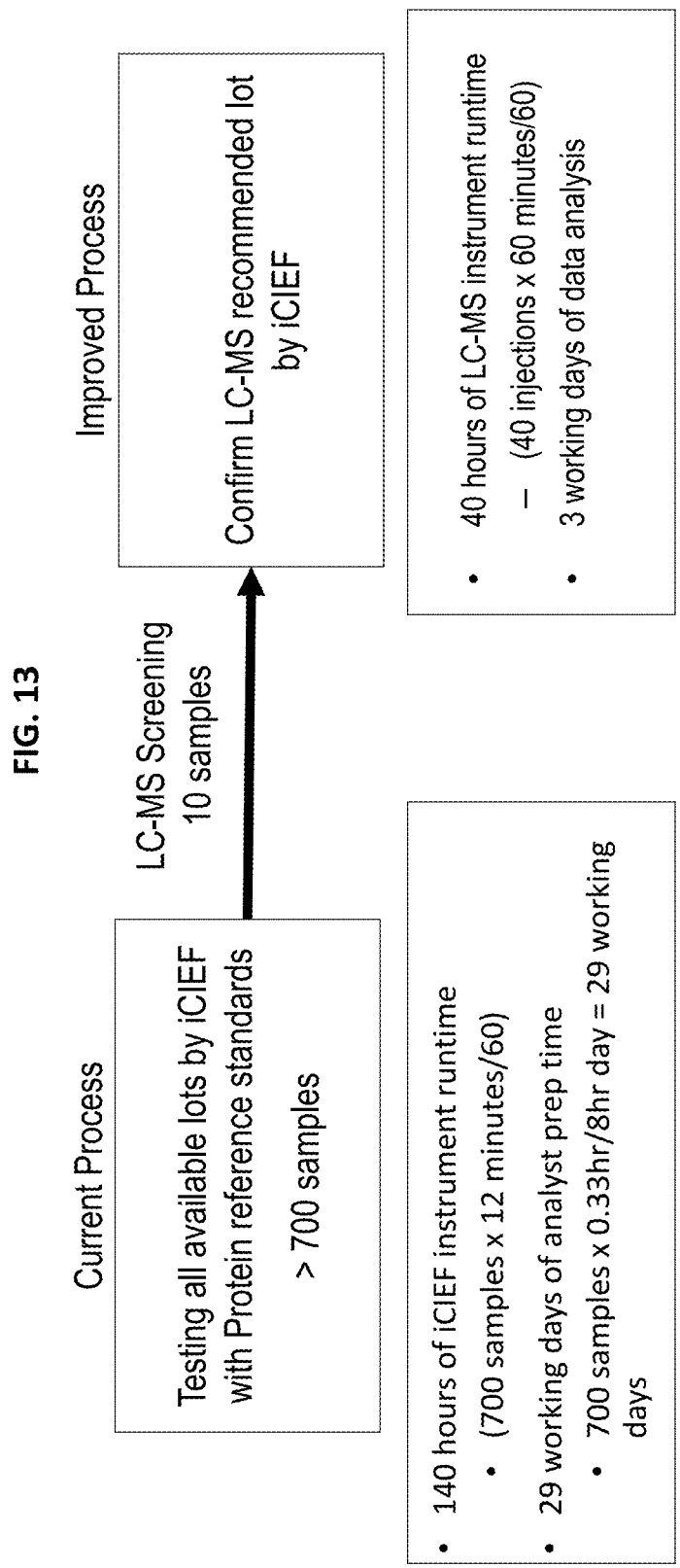
FIG. 13 is a diagram comparing the current ampholyte testing process with the new ampholyte testing methods described herein. The current methods reduce analysis time, as liquid chromatography-mass spectrometry (LC-MS) analysis of a new ampholyte lot takes 4 hours. Further the new ampholyte testing methods allow for ampholyte characterization without consuming any protein product. Lastly, the new ampholyte testing methods are applicable to any new ampholyte vendor. For each vendor, a new library of markers can be created using the methods described herein to compare ampholyte lots.

Furthermore, the extracted ion chromatogram (XIC) was monitored to verify a gaussian peak was observed (FIG. 11A). All markers that met the criteria were added to the screening library. This library was then used to evaluate which markers are present in which lots, and at what intensity. A heat map of the markers of interest was created where the internal standard normalized response in each lot was divided by the maximum normalized response across the 5 lots and multiplied by 100 to give a percentage (FIG. 10A). The trend observed in the heat map was supported by the results of the iCIEF testing. The greater the difference detected between the markers in lot 1 vs the other lots, the greater the electropherogram deviated from the SOP. Markers that were suspected to have a greater impact on assay performance were further investigated by elucidating the structure and performing a database search for identification (FIG. 12), using the UNIFI Scientific Information System based on elemental composition calculation, structural database search and fragment matching of the high collision energy data (see FIG. 12 for structures, FIG. 11A for an example chromatogram used in identification).

CONCLUSIONS

Characterizing ampholyte lot-to-lot variation using UPLC IMS-Q-ToF-MS was successful in predicting lot performance during iCIEF testing. This method will increase the efficiency of selecting new ampholyte lots, decrease the amount of iCIEF testing, and save reference standard protein. This same workflow can work for multiple materials and vendors if future lot-to-lot variation is observed.

What is claimed is:
1. A method of identifying an ampholyte composition for capillary isoelectric focusing (CIEF) or imaged capillary isoelectric focusing i (CIEF) of a protein sample, the method comprising:
   a. identifying at least one marker in at least one test ampholyte composition and in a reference ampholyte composition using liquid chromatography-mass spectrometry (LC-MS); and
   b. determining the degree of similarity or difference of the at least one marker between the at least one test ampholyte composition and the reference ampholyte composition, comprising:
      1. determining if the at least one marker has a low covariance and the level of the at least one marker is different between the at least one test ampholyte composition and the reference ampholyte composition, or
      2. determining if the at least one marker has a high covariance and the level of the at least one marker is similar between the at least one test ampholyte composition and the reference ampholyte composition;
   thereby identifying the ampholyte composition for CIEF or iCIEF of the protein sample.
2. The method of claim 1, wherein step (a) comprises
   i. determining Accurate Mass/Retention Time (AMRT) and/or collision cross section measurements for a plurality of components of the at least one test ampholyte composition and the reference ampholyte composition;
   ii. plotting covariance of the AMRT and/or collision cross section measurements for the plurality of components from the at least one test and reference ampholyte compositions using an S-plot; and
   iii. selecting at least one component that is different between the at least one test ampholyte composition and the reference ampholyte composition, wherein the difference comprises a covariance that is non-0 in the S-plot;
   thereby identifying the at least one marker.

3. The method of claim 2, wherein the at least one component comprises a covariance in the S-plot that is less than the covariance of at least 20%, at least 30%, at least 40%, at least 50%, at least 60%, at least 70%, or at least 80% of the plurality of components in the S-plot.

4. The method of claim 2 or 3, wherein the level of the at least one marker in the at least one test ampholyte composition and the reference ampholyte composition is different.

5. The method of claim 4, wherein the difference in the level of the at least one marker comprises a difference in level of at least 10%, at least 20%, at least 30%, at least 40%, at least 50%, at least 60%, at least 70%, at least 80%, or at least 90% relative to a normalized level of the at least one marker.

6. The method of claim 1, wherein step (a) comprises
 i. Determining Accurate Mass/Retention Time (AMRT) and/or collision cross section measurements for a plurality of components of the at least one test ampholyte composition and the reference ampholyte composition;
 ii. Plotting covariance of the AMRT and/or collision cross section measurements for the plurality of components from the at least one test and reference ampholyte compositions using an S-plot; and
 iii. selecting at least one component that is similar between the at least one test ampholyte composition and the reference ampholyte composition, wherein the similarity comprises a covariance that is non-0 in the S-plot;
thereby identifying the at least one marker.

7. The method of claim 6, wherein the at least one component comprises a covariance in the S-plot that is greater than the covariance of at least 40%, at least 50%, at least 60%, at least 70%, at least 80%, at least 90%, at least 95%, or at least 99% of the plurality of components in the S-plot.

8. The method of claim 6 or 7, wherein the level of the at least one marker in the at least one test ampholyte composition and the reference ampholyte composition is similar.

9. The method of claim 8, wherein the similarity in the level of the at least one marker comprises a level that is at least 20%, at least 30%, at least 40%, at least 50%, at least 60%, at least 70%, at least 80%, at least 90%, at least 95% or at least 99% similar relative to a normalized level of the at least one marker.

10. The method of claim 1, wherein the at least one marker is identified by a mass to charge ratio (m/z).

11. The method of claim 10, wherein the level of the at least one marker is characterized by relative intensity of the m/z in a mass spectrum.

12. The method of claim 11, wherein step (b) comprises:
 i. determining a LC-MS mass spectrum of the at least one marker in the at least one test ampholyte composition and the reference ampholyte composition,
 ii. determining the relative intensity of a base peak for the at least one marker in the mass spectrums of the at least one test ampholyte composition and the reference ampholyte composition,
 iii. normalizing the relative intensity of the base peak of the at least one marker to a maximum relative intensity of the base peak measured from the at least one test ampholyte composition or the reference ampholyte composition, and
 iv. comparing the normalized relative intensities of the base peak of the at least one marker in the at least one test and reference ampholyte compositions.

13. The method of claim 10, wherein the at least one marker comprises 1, 2, 3, 4, 5, 6, 7, 8, 9, 10, 11, 12, 13, 14, 15 or 16 markers with different m/z.

14. The method of claim 10, wherein the at least one marker comprises 16 markers with different m/z.

15. The method of claim 14, wherein the 16 markers comprise markers with an m/z of 280, an m/z of 319, an m/z of 329, an m/z of 347, an m/z of 373, an m/z of 375, an m/z of 376, an m/z of 431, an m/z of 504, an m/z of 506, an m/z of 508, an m/z of 520, an m/z of 534, an m/z of 562, an m/z of 906 and an m/z of 980.

16. The method of claim 1, wherein the mass spectrometry comprises ion mobility Quadrupole Time-of-flight Mass Spectrometry (IMS-Q-ToF-MS).

17. The method of claim 1, wherein the liquid chromatography comprises high-performance liquid chromatography (HPLC).

18. The method of claim 17, wherein the HPLC comprises a C4 silica column.

19. The method of claim 1, further comprising validating the at least one test ampholyte composition by generating an imaged capillary isoelectric focusing (iCIEF) electropherogram of a reference protein using the reference ampholyte composition and the at least one test ampholyte composition, thereby generating at least one test electropherogram and a reference electropherogram.

20. The method of claim 19, wherein the test ampholyte composition is validated if the at least one test and the reference electropherograms are similar.

21. The method of claim 20, wherein the similarity of the at least one test and reference electropherograms is determined by number, size, or isoelectric point (pI) of peaks, or a combination thereof.

22. The method of claim 20 or 21, wherein the similarity of the at least one test and reference electropherograms comprises having an identical number of peaks.

23. The method of claim 20, wherein the similarity of the at least one test and reference electropherograms comprises a difference in an area under the peak of a region of the reference and at least one test electropherograms with a p-value of less than 0.05.

24. The method of claim 23, wherein the region comprises a major reference peak, a region that is more acidic than the major reference peak, or a region that is more basic than the major reference peak.

25. The method of claim 1, wherein the iCIEF is used to characterize a protein drug product or drug substance.

\* \* \* \* \*

UNITED STATES PATENT AND TRADEMARK OFFICE
CERTIFICATE OF CORRECTION

| | |
|---|---|
| PATENT NO. | : 12,055,518 B2 |
| APPLICATION NO. | : 17/067044 |
| DATED | : August 6, 2024 |
| INVENTOR(S) | : Rachel Mullen et al. |

It is certified that error appears in the above-identified patent and that said Letters Patent is hereby corrected as shown below:

In the Claims

At Column 26, Claim 1, Line 32:
"isoelectric focusing i (CIEF) of a protein sample,"
Should read:
--isoelectric focusing i(CIEF) of a protein sample,--

At Column 27, Claim 10, Line 46:
"marker is identified by a mass to charge ratio (m/z)."
Should read:
--marker is identified by a mass to charge ratio ($m/z$).--

At Column 27, Claim 11, Line 49:
"m/z in a mass spectrum."
Should read:
--$m/z$ in a mass spectrum.--

At Column 28, Claim 13, Line 11:
"15 or 16 markers with different m/z."
Should read:
--15 or 16 markers with different $m/z$.--

At Column 28, Claim 14, Line 13:
"marker comprises 16 markers with different m/z."
Should read:
--marker comprises 16 markers with different $m/z$.--

Signed and Sealed this
Third Day of September, 2024

*Katherine Kelly Vidal*
Katherine Kelly Vidal
*Director of the United States Patent and Trademark Office*

At Column 28, Claim 15, Lines 15-19:
"comprise markers with an m/z of 280, an m/z of 319, an m/z of 329, an m/z of 347, an m/z of 373, an m/z of 375, an m/z of 376, an m/z of 431, an m/z of 504, an m/z of 506, an m/z of 508, an m/z of 520, an m/z of 534, an m/z of 562, an m/z of 906 and an m/z of 980."
Should read:
--comprise markers with an *m/z* of 280, an *m/z* of 319, an *m/z* of 329, an *m/z* of 347, an *m/z* of 373, an *m/z* of 375, an *m/z* of 376, an *m/z* of 431, an *m/z* of 504, an *m/z* of 506, an *m/z* of 508, an *m/z* of 520, an *m/z* of 534, an *m/z* of 562, an *m/z* of 906 and an *m/z* of 980.--